(12) United States Patent
Gemer et al.

(10) Patent No.: US 11,083,484 B2
(45) Date of Patent: Aug. 10, 2021

(54) MEDICAL DEVICE FOR TREATMENT OF A SINUS AND/OR AN EAR AND METHODS OF USE THEREOF

(71) Applicant: SINUSAFE MEDICAL LTD., Kiryat Ono (IL)

(72) Inventors: Avinoam Gemer, Kiryat Ono (IL); Nir Altman, Kfar Etsyon (IL); Raphael Meloul, Shilo (IL)

(73) Assignee: SINUSAFE MEDICAL LTD., Kiryat Ono (IL)

( * ) Notice: Subject to any disclaimer, the term of this patent is extended or adjusted under 35 U.S.C. 154(b) by 50 days.

(21) Appl. No.: 16/313,246

(22) PCT Filed: Jul. 3, 2017

(86) PCT No.: PCT/IL2017/050744
§ 371 (c)(1),
(2) Date: Dec. 26, 2018

(87) PCT Pub. No.: WO2018/008020
PCT Pub. Date: Jan. 11, 2018

(65) Prior Publication Data
US 2019/0290314 A1 Sep. 26, 2019

Related U.S. Application Data

(60) Provisional application No. 62/358,017, filed on Jul. 3, 2016, provisional application No. 62/393,317, filed
(Continued)

(51) Int. Cl.
*A61B 17/3207* (2006.01)
*A61B 17/24* (2006.01)
(Continued)

(52) U.S. Cl.
CPC .......... *A61B 17/3207* (2013.01); *A61B 17/24* (2013.01); *A61M 25/0113* (2013.01);
(Continued)

(58) Field of Classification Search
CPC .............. A61M 29/00; A61M 25/0113; A61M 25/0136; A61B 1/00; A61B 17/24;
(Continued)

(56) References Cited

U.S. PATENT DOCUMENTS

| 400,589 A | 4/1889 | Molesworth |
|---|---|---|
| 2,525,183 A | 3/1947 | Robison |

(Continued)

FOREIGN PATENT DOCUMENTS

| CN | 102512271 | 6/2012 |
|---|---|---|
| CN | 102525703 | 7/2012 |

(Continued)

OTHER PUBLICATIONS

International Search Report PCT/IL2017/050744 Completed Sep. 28, 2017; dated Sep. 28, 2017 15 pages.
(Continued)

*Primary Examiner* — George J Ulsh
(74) *Attorney, Agent, or Firm* — The Roy Gross Law Firm, LLC; Roy Gross

(57) ABSTRACT

There is provided herein, a device for treating and/or diagnosing a sinus or an ear condition, the device comprising a housing comprising or functionally connected to: a hollow cannula defining a lumen extending at least partially along the length thereof, the cannula is configured to be at least partially inserted through an ostium into a sinus cavity/ear of a subject; and a flexible grinding wire movable within the cannula's lumen and configured to be inserted into and retrieved out of the sinus cavity through the cannula's lumen, and to rotate along a longitudinal axis thereof and
(Continued)

thereby grind, chop and/or stir material present in the sinus cavity and/or inside the hollow cannula, wherein the cannula is in fluid flow communication with an irrigation/aspiration source; and a wire handle functionally connected to the wire, allowing a user to advance and retrieve the wire within the cannula and into and out of the cannula lumen, wherein the device is handheld by a gripping handle.

17 Claims, 15 Drawing Sheets

Related U.S. Application Data on Sep. 12, 2016, provisional application No. 62/487,122, filed on Apr. 19, 2017.

(51) Int. Cl.
*A61M 29/00* (2006.01)
*A61M 25/01* (2006.01)
*A61B 17/00* (2006.01)
*A61B 17/32* (2006.01)

(52) U.S. Cl.
CPC ........ *A61M 25/0136* (2013.01); *A61M 29/00* (2013.01); *A61B 2017/0046* (2013.01); *A61B 2017/00787* (2013.01); *A61B 2017/320008* (2013.01); *A61B 2017/320733* (2013.01); *A61B 2217/005* (2013.01); *A61B 2217/007* (2013.01)

(58) Field of Classification Search
CPC ........ A61B 17/3207; A61B 2017/0046; A61B 2017/00787; A61B 2017/320008; A61B 2017/320733; A61B 2217/005; A61B 2217/007
See application file for complete search history.

(56) References Cited

U.S. PATENT DOCUMENTS

| | | |
|---|---|---|
| 5,087,265 A | 2/1992 | Summers |
| 5,685,838 A | 11/1997 | Peters et al. |
| 5,957,881 A | 9/1999 | Peters et al. |
| 6,042,593 A | 3/2000 | Storz et al. |
| 6,042,598 A | 3/2000 | Tsugita et al. |
| 6,090,118 A | 7/2000 | McGuicken, Jr. |
| 6,174,280 B1 * | 1/2001 | Oneda ................ A61B 1/00078 600/114 |
| 6,293,957 B1 | 9/2001 | Peters et al. |
| 6,319,242 B1 | 11/2001 | Patterson et al. |
| 6,375,634 B1 | 4/2002 | Carroll |
| 6,471,679 B1 | 10/2002 | Suh |
| 7,678,099 B2 | 3/2010 | Ressemann et al. |
| 7,785,337 B2 | 8/2010 | Adams et al. |
| 8,343,179 B2 | 1/2013 | To et al. |
| 8,465,508 B2 | 6/2013 | Tal |
| 8,597,203 B2 | 12/2013 | Flatland et al. |
| 8,721,591 B2 | 5/2014 | Chang et al. |
| 8,801,738 B2 | 8/2014 | Yoon et al. |
| 2002/0133111 A1 | 9/2002 | Shadduck |
| 2003/0191474 A1 | 10/2003 | Cragg et al. |
| 2006/0004323 A1 | 1/2006 | Chang et al. |
| 2007/0239109 A1 | 10/2007 | Dareuil |
| 2007/0264342 A1 | 11/2007 | Oliver et al. |
| 2008/0027423 A1 | 1/2008 | Choi et al. |
| 2008/0097516 A1 | 4/2008 | Chang et al. |
| 2008/0275483 A1 | 11/2008 | Makower et al. |
| 2008/0281156 A1 | 11/2008 | Makower et al. |
| 2009/0258330 A1 | 10/2009 | Huber et al. |
| 2010/0030113 A1 | 2/2010 | Morriss et al. |
| 2010/0076476 A1 | 3/2010 | To et al. |
| 2010/0204773 A1 | 8/2010 | Elmaleh et al. |
| 2011/0160740 A1 | 6/2011 | Makower et al. |
| 2011/0201996 A1 | 8/2011 | Melder |
| 2011/0282251 A1 | 11/2011 | Baker et al. |
| 2011/0288477 A1 | 11/2011 | Ressemann et al. |
| 2013/0012869 A1 | 1/2013 | Cha et al. |
| 2013/0023894 A1 | 1/2013 | Saleh |
| 2013/0023895 A1 | 1/2013 | Saleh |
| 2013/0046316 A1 | 2/2013 | Sullivan et al. |
| 2013/0053824 A1 | 2/2013 | Seiden et al. |
| 2013/0165873 A1 | 6/2013 | Morriss et al. |
| 2013/0184574 A1 | 7/2013 | Newhauser, Jr. et al. |
| 2013/0211321 A1 | 8/2013 | Dubois et al. |
| 2013/0225937 A1 | 8/2013 | Schaeffer et al. |
| 2013/0226070 A1 | 8/2013 | Solem |
| 2013/0253387 A1 | 9/2013 | Bonutti et al. |
| 2013/0282113 A1 | 10/2013 | Punga et al. |
| 2013/0310734 A1 | 11/2013 | Biel et al. |
| 2014/0012309 A1 | 1/2014 | Keith et al. |
| 2014/0276626 A1 | 9/2014 | Jenkins et al. |
| 2014/0276654 A1 | 9/2014 | Jenkins |
| 2014/0277043 A1 | 9/2014 | Jenkins et al. |

FOREIGN PATENT DOCUMENTS

| | | |
|---|---|---|
| CN | 202505522 | 10/2012 |
| CN | 203001031 | 6/2013 |
| CN | 203139339 | 8/2013 |
| JP | 2001510068 A | 7/2001 |
| JP | 2007521916 A | 8/2007 |
| JP | 2009505691 A | 2/2009 |
| KR | 101179692 | 9/2012 |
| WO | 82004388 | 12/1982 |
| WO | 9904701 | 2/1999 |
| WO | 2005077284 A2 | 8/2005 |
| WO | 2006015111 | 2/2006 |
| WO | 2012052827 | 4/2012 |
| WO | 2014072977 | 5/2014 |
| WO | 2016110854 | 7/2016 |

OTHER PUBLICATIONS

Written Opinion of the International Searching Authority PCT/IL2017/050744 dated Sep. 28, 2017 6 pages.

* cited by examiner

MEDICAL DEVICE FOR TREATMENT OF A SINUS AND/OR AN EAR AND METHODS OF USE THEREOF

RELATED APPLICATIONS

This application is a National Phase of PCT Patent Application No. PCT/IL2017/050744 having an International filing date of Jul. 3, 2017, which claims the benefit of priority of U.S. Provisional Application No. 62/358,017 filed on Jul. 3, 2016, U.S. Provisional Application No. 62/393,317 filed on Sep. 12, 2016, and U.S. Provisional Application No. 62/487,122 filed on Apr. 19, 2017. The contents of the above applications are all incorporated by reference as if fully set forth herein in their entirety.

TECHNICAL FIELD

The present disclosure generally relates to the field of devices and methods for treatment and/or diagnosis of sinus conditions.

BACKGROUND

Paranasal sinus conditions such as sinusitis, annually affects nearly 35 million patients in the United States alone. It can be due to infection, allergy or autoimmune problems, with a majority of cases being due to a viral infection, aerobes bacteria and anaerobes bacteria. The exact cause of sinusitis might be unclear to a health care provider as symptoms may be undistinguishable. Facing this uncertainty, the treatment of the condition is commonly carried out by administering various medications and/or providing various treatments thus determining the actual cause through a method of elimination of potential causes. As a result, the patient may be exposed to unnecessary drugs or procedures.

Another possibility is to surgically penetrate the paranasal sinus by puncturing through the paranasal sinus bones or by breaking the bones around the paranasal sinus natural opening for taking samples and determining the cause of the condition. Treatment can be administered during such surgery, for example by a process known as lavage or irrigation and aspiration. Many complications are associated with these surgical options; therefore, health providers tend to be reluctant in executing them unless necessity calls for it in acute cases.

There is thus a need in the art to provide devices, systems and methods allowing diagnosis and treatment of paranasal sinus conditions, without exposing the patient to unnecessary medication and/or massively invasive surgical intervention.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

According to some embodiments, there are provided herein devices, systems and methods for treating and/or diagnosing a sinus (such as a paranasal sinus) and/or an ear condition using a hollow cannula which may access the sinus/ear through the natural opening, thereby facilitating diagnosis and/or treatment of the sinus conditions without a surgical dilation or an expansion.

According to some embodiments, there is provided herein a medical device for treating and/or diagnosing a sinus and/or ear condition, the medical device comprising: a housing comprising or functionally connected to: a hollow cannula defining a lumen extending at least partially along the length thereof, the cannula is configured to be at least partially inserted through an ostium into a sinus cavity/ear of a subject; and a flexible grinding wire movable within the cannula's lumen and configured to be inserted into and retrieved out of the sinus cavity through the cannula's lumen, and to rotate along a longitudinal axis thereof and thereby grind, chop and/or stir material present in the sinus cavity and/or inside the hollow cannula, wherein the cannula is in fluid flow communication with an irrigation/aspiration source; and a wire handle functionally connected to the wire, allowing a user to advance and retrieve the wire within the cannula and into and out of the cannula lumen, wherein the device is handheld by a gripping handle.

According to some embodiments, there is provided herein a medical kit for treating and/or diagnosing a sinus or an ear condition, the kit comprising: a device comprising: a housing comprising or functionally connected to: a hollow cannula defining a lumen extending at least partially along the length thereof, the cannula is configured to be at least partially inserted through an ostium into a sinus cavity/ear of a subject; and a flexible grinding wire movable within the cannula's lumen and configured to be inserted into and retrieved out of the sinus cavity through the cannula's lumen, and to rotate along a longitudinal axis thereof and thereby grind, chop and/or stir material present in the sinus cavity and/or inside the hollow cannula, wherein the cannula is in fluid flow communication with an irrigation/aspiration source; a wire handle functionally connected to the wire, allowing a user to advance and retrieve the wire within the cannula and into and out of the cannula lumen; and a guiding tube configured to house the cannula therein and bend the cannula as it is being advanced forward, and direct a distal end of the cannula towards a sinus opening, wherein the device is handheld by a gripping handle; a connector configured for replacing of guiding tubes; and a set of replaceable guiding tubes having different angles at a distal section thereof for fitting to different sinus anatomies.

According to some embodiments, the device may further include a cannula handle functionally connected to the cannula, allowing a user to advance and retrieve the cannula into a sinus cavity or an ear.

According to some embodiments, the device may further include a guiding tube configured to house the cannula therein and bend the cannula as it is being advanced forward, and direct a distal end of the cannula towards a sinus (or an ear) opening.

According to some embodiments, the device may further include a curve in the cannula distal tip and a cannula rotating mechanism, configured to allow the user to rotate a distal tip of the cannula around a longitudinal axis of the cannula, thus facilitate insertion of the cannula into the sinus cavity. The cannula's rotating mechanism may include a dial allowing the user to rotate the distal tip of the cannula, for example, with the same hand, which is holding the device.

According to some embodiments, the device may further include a connector configured for replacing of (e.g., disposable) guiding tubes.

According to some embodiments, the device may further include a mechanism for changing an angle of a distal section of the guiding tube, to facilitate introduction of the cannula to various sinus anatomies.

According to some embodiments, the device may further include a shaft, wherein at a distal section thereof, the shaft is connected to the wire and at a proximal section thereof, the shaft is connected to a motor connected to the wire handle, wherein the motor provides rotational movement to the shaft, which transmits this movement to the wire. According to some embodiments, the motor itself is the wire handle. According to some embodiments, the wire directly connects to the motor, without a shaft. According to some embodiments, the wire handle protects the user from touching the wire and facilitates distal and proximal movement of the wire while the wire is rotating.

According to some embodiments, the motor may be configured to be at least partially within the device body. The motor and the device body may be detachably connectable.

According to some embodiments, the device may further include a liquid tube connected at a distal section thereof to a proximal side of the cannula and at a proximal section thereof to the irrigation/aspiration source, such that the liquid tube is in fluid flow connection with the cannula and the irrigation/aspiration source, wherein an inner diameter of the liquid tube is larger than an inner diameter of the cannula, and wherein at least part of the shaft is located within the liquid tube lumen. According to some embodiments, the shaft may be supported within the liquid tube by one or more mechanisms that are configured to reduce a friction and/or vibration between the shaft and the liquid tube. According to some embodiments, a distal end of the shaft and/or a proximal end of the liquid tube comprise a mechanism configured to prevent liquid occlusion in the cannula and/or the liquid tube when the shaft is being advanced distally toward a connection point between the cannula and the liquid tube.

According to some embodiments, the irrigation/aspiration source may include a replaceable syringe, a syphon, and/or a liquid container.

According to some embodiments, the device may further include a cannula/liquid tube seal located within a defined lumen within the housing and surrounding at least portion of the cannula/liquid tube, such that the cannula/liquid tube is distally/proximally movable within the lumen and relative to the handle grip while remaining the cannula/liquid tube cavity sealed from air inlet and liquid outlet during irrigation and aspiration. The cannula/liquid tube seal may further be configured to facilitate rotation of the cannula/liquid tube relative to the handle grip while the cannula/liquid tube remains sealed.

According to some embodiments, the device may further include a wire/shaft seal surrounding at least a portion of the wire/shaft and facilitating distal/proximal movement of the wire/shaft within and relative to the cannula/liquid tube, while maintaining the cannula/liquid tube sealed from air inlet and liquids outlet during irrigation and aspiration. The wire/shaft seal may further be configured to facilitate high RPM rotation of the wire/shaft within and relative to the cannula/liquid tube, while the cannula/liquid tube remains sealed.

According to some embodiments, the device may further include an irrigation/aspiration seal configured for connection and/or detachment of the irrigation/aspiration source to the liquid tube/cannula in a sealed manner.

According to some embodiments, the device may further include a cannula position marking configured to provide the user indication about the cannula's distal end location and/or orientation in relation to a sinus opening.

According to some embodiments, the device may further include a wire position marking configured to provide the user indication about the wire's distal end location and/or orientation in relation to the cannula's distal end.

According to some embodiments, the device may further include a connector connecting between the liquid tube/cannula and the shaft/wire such that when the liquid tube/cannula is moved distally the shaft/wire will also be distally moved, for at least part of the liquid tube/cannula advancement.

According to some embodiments, the device may further include a locking mechanism for locking the cannula at a certain position. The locking mechanism may be manually or automatically operable and is located in or connected to the cannula handle.

According to some embodiments, the device may further include a side port in the guiding tube, wherein the side port is configured for instrumentation insertion through a distal end of the guiding tube. The side port may be configured to serve as an aspiration port in fluid flow connection with a distal end of the guiding tube, wherein the aspiration port is configured for suction of aspiration/irrigation fluid from the guiding tube. The aspiration port may be connectable to a suction machine.

According to some embodiments, the gripping handle is essentially perpendicular to the longitudinal axis of the device. According to some embodiments, the irrigation/aspiration source may be at least partially housed within the gripping handle.

According to some embodiments, the device may further include a hollow trocar configured to house the cannula therein, puncture a sinus wall, sinus floor or ear wall and facilitate insertion of the cannula into the sinus/ear cavity. The cannula may be configured to puncture via an ear or a sinus wall or sinus floor as a trocar. According to some embodiments, the device may further include a spring activated mechanism configured to control and limit the trocar puncturing movement. A distal end of the trocar may be configured to irrigate or aspirate liquids through a lumen thereof to/from an irrigation/aspiration source connected proximally to the trocar distal end. According to some embodiments, the terms "trocar" and "needle" may be used interchangeably.

According to some embodiments, the terms "ostium", "opening" and "natural opening" may be used interchangeably.

According to some embodiments, the cannula may be configured to be inserted into a sinus cavity or an ear cavity through an endoscope working channel. According to some embodiments, the cannula (for example, a stiff or a flexible cannula) and the wire may be configured to be inserted into a sinus cavity or an ear cavity through an endoscope working channel. According to some embodiments, the endoscope itself is configured to enter the sinus cavity or an ear cavity and the wire is configured to be inserted into a sinus cavity or an ear cavity through the endoscope working channel.

According to some embodiments, the device may further include a sinus opening dilation mechanism, mounted on a distal end of the cannula.

According to some embodiments, the cannula may be a rigid bent (curved) cannula, configured to be inserted into the sinus cavity. According to some embodiments, the device may further include a tubular member surrounding the bent cannula, a distal end of the tubular member is configured to face a sinus or ear opening and to irrigate and/or aspirate liquid through the tube to an irrigation/aspiration source connected to the tubular member proximally to its distal end. According to some embodiments, the bent cannula may be inserted into a sinus cavity, a first irrigation aspiration source irrigates the sinus via the cannula, while the wire is rotating within the sinus or the ear cavity, and a second irrigation/aspiration source aspirates the irrigation out of the sinus or ear opening.

According to some embodiments, the device may further include visualization equipment located within or mounted on a distal tip of the guiding tube. According to some embodiments, the device may further include a visualization equipment attachment mechanism located within or mounted on a distal tip of the guiding tube.

According to some embodiments, there is provided herein a method for treating and/or diagnosing a sinus or an ear condition, the method comprising: utilizing a device comprising a housing comprising or functionally connected to: a hollow cannula defining a lumen extending at least partially along the length thereof, the cannula is configured to be at least partially inserted through an ostium into a sinus cavity/ear of a subject; and a flexible grinding wire movable within the cannula's lumen and configured to be inserted into and retrieved out of the sinus cavity through the cannula's lumen, and to rotate along a longitudinal axis thereof and thereby grind, chop and/or stir material present in the sinus cavity and/or inside the hollow cannula, wherein the cannula is in fluid flow communication with an irrigation/aspiration source; a wire handle functionally connected to the wire, allowing a user to advance and retrieve the wire within the cannula and into and out of the cannula lumen; and a guiding tube configured to house the cannula therein and bend the cannula as it is being advanced forward, and direct a distal end of the cannula towards a sinus opening, wherein the device is handheld by a gripping handle, advancing a distal end of the guiding tube towards the ostium; operating the cannula handle to advance the cannula within a guiding tube and through the ostium into a cavity of the sinus/ear; operating the wire handle to distally advance the wire out of the cannula and into the sinus cavity; and activating the motor to induce rotation of the wire. The method may further include providing irrigation fluid to the sinus cavity via the cannula.

According to some embodiments, the device cannula is not movable and not flexible, as described above, but stiff and fixed. According to those embodiments the cannula will be described as a tubular member with a distal curved end. According to some embodiments, the curved distal end is intended to be inserted into patient sinus. According to some embodiments, the curved distal end is configured to be inserted into the maxillary sinus. According to some embodiments, the curved distal end is configured to be inserted into the frontal sinus. According to some embodiments, the curved distal end is configured to be inserted into the sphenoid sinus. According to some embodiments, the curved distal end is configured to be inserted into the ear Eustachian tube. According to some embodiments, the curved distal end might have angles of 110-90 for the maxillary sinus, 0-30 for the sphenoid sinus, 60-80 for the frontal sinus, 30-70 for the Eustachian tubes. According to some embodiments, the distal end might be bendable or malleable. According to some embodiments, it might be bendable by the user hands, and according to others it may be bendable using a bending jig.

According to some embodiments, the curved distal end comprises an atraumatic tip. According to some embodiments, the atraumatic tip has a round or a ball shape. According to some embodiments, the atraumatic tip and or curved distal end has one or more holes for irrigation and or aspiration. According to some embodiments, at least some of the holes are side holes. According to some embodiments, the atraumatic tip contains a guide wire, a lens, a light source, a camera or any combination thereof.

According to some embodiments, the rotating wire is capable of rotating inside the curved distal end during sinus irrigation via the curved distal end. According to some embodiments, the rotating wire is capable of rotating inside the curved distal end during sinus irrigation and sinus aspiration via the curved distal end. According to some embodiments, the rotating wire protrudes out of the curved distal end. According to some embodiments, the rotating wire protrudes out of the atraumatic tip. According to some embodiments, the rotating wire protrudes out of the curved distal end or atraumatic tip is side protrusion.

According to some embodiments, the device's tubular member is within an aspiration tube. The aspiration tube has a proximal end and distal end. At least a part of the tubular member distal curved end is not covered by the aspiration tube. According to some embodiments, the tubular member distal curved end is capable of being at least partially inserted into a patient's sinus or Eustachian tube, while the aspiration tube is not inserted into the sinus or Eustachian tube. According to some embodiments, the tubular member distal curved end is capable of providing irrigation and or aspiration while the aspiration tube is aspirating the liquids spilled out of the sinus. According to some embodiments, the tubular member distal curved end is capable of providing irrigation and or aspiration while the rotating wire is rotating within the tubular member distal curved end and or within the sinus and while the aspiration tube is aspirating the liquids spilled out of the sinus. According to some embodiments, the aspiration tube is connected to an aspiration machine or to a syringe. According to some embodiments, the aspiration tube or the connector has a T or Y shape and it has a connection to a suction machine or a syringe via the aspiration tube. According to some embodiments, the aspiration tube or the connector or a proximal aspiration tubing has a syphon mechanism to collect aspirated liquids or specimens from the sinus. According to some embodiments, the aspiration tube distal end is atraumatic. According to some embodiments, the aspiration tube distal end is made of soft material and or collapsible construction such as foam. According to some embodiments, the soft material and or collapsible construction such as foam, circumference the distal end of the tube. According to some embodiments, the soft material and or collapsible construction such as foam has a ring shape and it is located proximally to the aspiration tube distal end. According to some embodiments, a ring may be attached to the sinus ostium during sinus irrigation and aspiration. According to some embodiments, the ring may seal the sinus opening during irrigation and may prevent irrigation liquid flow from the sinus to the nasal cavity.

According to some embodiments, the device is configured to be inserted into a sinus cavity via an endoscope. According to some embodiments, the device is configured to be inserted into a sinus cavity via an endoscope working channel. According to some embodiments, the endoscope is a flexible endoscope. According to some embodiments, the flexible endoscope comprises actuation mechanisms that allow the user to control its distal tip curve.

According to some embodiments, the device is configured such as that the endoscope working channel might replace or serve as the guiding tube. According to those embodiments, the cannula might be inserted into an endoscope inner lumen and into the sinus cavity. According to those embodiments, the cannula and wire actuation and sealing mechanisms will be as described above.

According to some embodiments, the device is configured such that the endoscope working channel might replace or serve as the cannula and or the liquid tube. According to those embodiments, the wire might be inserted into an endoscope inner lumen and into the sinus cavity. According to those embodiments, the wire actuation and sealing mechanisms will be as described above.

According to some embodiments, the device guiding tube or cannula might comprise: a straight support element having a first rigidity; a curved support element, slideably coupled to the straight support element, the curved support element having a curved portion, the curved portion of the curved support element having a second rigidity greater than the first rigidity, at least the curved portion having rectangular cross section; and a rigid straight support element slideably coupled to the curved support element, the rigid straight support element having a third rigidity greater than the second rigidity, when the rigid straight support element overlaps the curved portion of the curved support element, an overlapped portion of the curved portion conforms to a straight shape of the rigid straight support element, and when the curved portion overlaps the straight support element, an overlapped portion of the straight support element conforms to a curved shape of the curved portion. According to some embodiments, such endoscope is comprised of least one work channel.

According to some embodiments, the device guiding tube or cannula might comprise: a first support element configured to move from a substantially straight configuration to a curved configuration defining a radius of curvature, the first support element having a rectangular cross section; a second support element configured to slideably move relative to the first support element such that when the second support element overlaps the first support element, the first support element is in its straight configuration; and a third support element, at least a portion of which is configured to have the radius of curvature of the first support element when it overlaps the first support element. According to some embodiments, such endoscope includes at least one work channel.

According to some embodiments, the movable seal, that keeps the liquid tube sealed despite the liquid tube movement backward and forward, may be replaced by a part of the liquid tube that is expandable, such as expandable tubing. According to some embodiments, the expandable part of the liquid tube can rotate and transmit torque in order to connect between the cannula and the dial, such as the movable seal. According to some embodiments, the expandable part comprises support, such as a spring, or a spiral spring, to transmit the rotation from the dial to the cannula.

According to some embodiments, the device comprises a manual rotation mechanism instead of a motor. According to some embodiments, the manual rotation mechanism may include any mechanism for manually spinning the shaft.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

More details and features of the current invention and its embodiments may be found in the description and the attached drawings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1A:
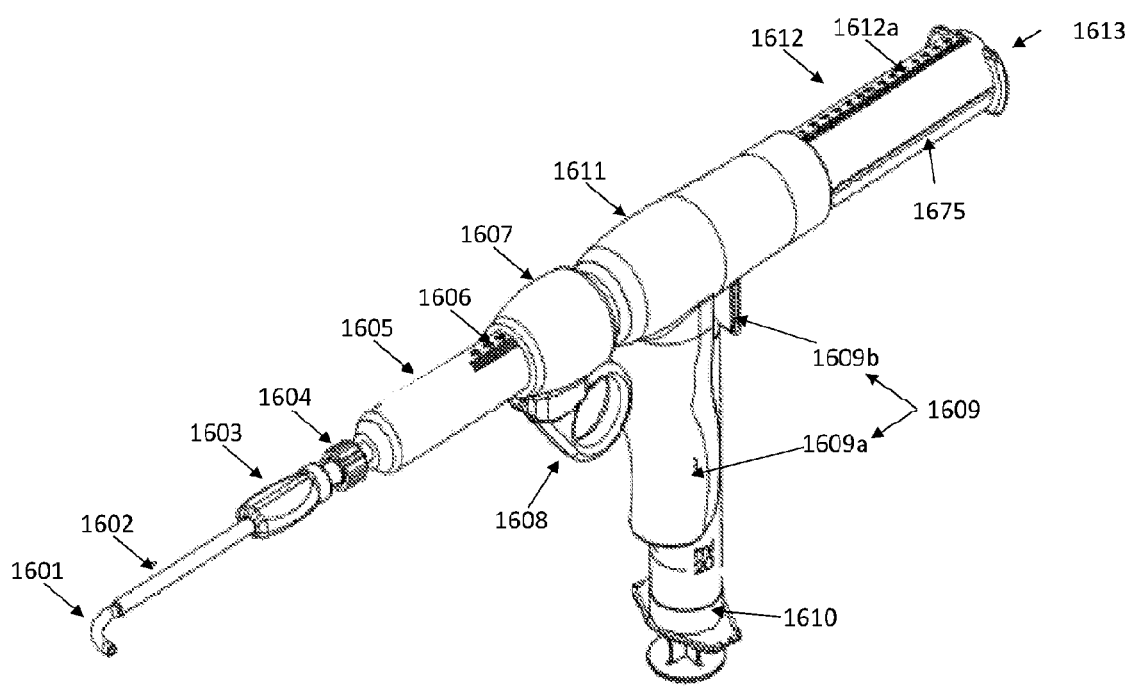
FIGS. 1A and 1B schematically illustrate a device for treating a paranasal sinus condition in retracted and opened configurations, respectively, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a medical device for treating and/or diagnosing a paranasal sinus condition. As used herein, the term "paranasal sinus" refers to an air-filled space that surrounds the nasal cavity. The paranasal sinuses include, but are not limited to the area located under the eyes; the frontal sinuses above the eyes; the ethmoidal sinuses between the eyes; the sphenoidal sinuses behind the eyes, and the middle ear cavity.

According to some embodiments, there are provided herein devices, systems and methods for treating and/or diagnosing paranasal sinus conditions using a hollow cannula which may access the paranasal sinus through the natural paranasal sinus opening, thereby facilitating diagnosis and/or treatment of the paranasal sinus conditions without surgical puncturing, dilation or expansion.

There is provided, according to some embodiments, a device for diagnosis and/or treatment of paranasal conditions including a flexible hollow cannula configured to be inserted to a paranasal sinus through a natural opening thereof. The flexible hollow cannula is shaped to reach a desired treatment area within the paranasal sinus. The flexible hollow cannula is at least partially housed in and movable within a guiding tube with a bent/bendable distal end configured to be inserted to a nasal cavity through a nostril, such as to face a natural opening of a paranasal sinus.

During a treatment and/or a diagnosis procedure, a healthcare provider may introduce the distal end of the guiding tube to the nasal cavity of a subject. A distal portion of the guiding tube may be bent so as to face a natural opening of a paranasal sinus. Alternatively, the distal portion of the guiding tube includes a predefined bent allowing it to face a natural opening of a paranasal sinus. The flexible hollow cannula may protrude distally from the guiding tube into the natural opening to the paranasal sinus. According to some embodiments, when the protruding portion or the hollow shaft is extended, it assumes a relaxed shape that allows reaching a treatment area within the paranasal sinus.

According to some embodiments, the flexible hollow cannula may be configured to penetrate through and/or be inserted into the ostium without requiring prior surgical dilation or expansion. That is, the flexible hollow cannula may be sized and shaped to enter the sinus through a natural sized opening thereof. According to some embodiments, the hollow cannula may have an external diameter of 2.5 mm or below, 2.0 mm or below, 1.5 mm or below, 1.3 mm or below, 1.2 mm or below, 1.1 mm or below, or 1 mm or below. Each possibility represents a separate embodiment.

According to some embodiments, the flexible hollow cannula houses a grinding wire configured to grind, chop and/or stir mucus material. As used herein the term "mucus material" may refer to mucus, fungus, bacteria, biofilm, soft polyps, mucusal soft tissue, irrigation fluids or any other material or combination of materials present in the sinus cavity and/or within the hollow cannula.

According to some embodiments, the wire is connected to a motor. According to some embodiments, the wire and the motor are interconnected by a transmission shaft ("shaft"). Optionally, a proximal end of the wire is coupled to a distal portion of the transmission shaft. According to some embodiments, a proximal end of the transmission shaft is connected directly to the motor. Alternatively or additionally, the proximal end of the transmission shaft is connected to a motor gear. In some embodiments, the transmission shaft may be a plastic or metal rod or tube such as a steel rod. According to some embodiments, the transmission shaft includes more than one shaft. According to some embodiments, the transmission shaft comprises a gear. According to some embodiments, the transmission shaft is supported by one or more bearings. According to some embodiments, the transmission shaft is supported by a plurality of bearings. According to some embodiments, the transmission shaft may be advanced and retrieved through the plurality of bearings.

According to some embodiments, the device includes a casing having a distal end and a proximal end. According to some embodiments, the device's casing distal end is connected to the tubular member. According to some embodiments, the casing includes within it at least one of the following: a cannula, a liquid tube, a wire, a wire transmission mechanism, a syringe/irrigation/suction connector, and a motor connector. According to some embodiments, the casing houses within it at least a portion of the motor. According to some embodiments, the casing houses within it or is coupled to an irrigation and/or aspiration mechanism. According to some embodiments, the irrigation and/or aspiration mechanism includes a syringe. According to some embodiments, the irrigation and/or aspiration mechanism is motorized.

According to some embodiments, a Y or a T connector interconnects the wire transmission and the liquid tube to the cannula. The connection between the Y or T connector to the cannula may be direct or via a liquid tube. Non-limiting examples of liquid tubes include plastic or metal tubing such as a steel tube. According to some embodiments, the liquid tube houses at least part of the wire transmission and the wire. According to some embodiments, the liquid tube is coupled to the guiding tube or the tubular member. According to some embodiments, the liquid tube is coupled to the tubular member and to the cannula.

According to some embodiments, the casing includes a gripping handle which may enable a user (such as a doctor, nurse or a technician) to hold the device. According to some embodiments, a gripping handle enables the user to hold the device in a pencil like grip. According to some embodiments, the gripping handle is fitted to contain a syringe within it, or at least partially within it. According to some embodiments, the casing is fitted to contain a syringe within it, or at least partially within it. According to some embodiments, the gripping handle or casing is fitted only for a certain size syringe. That way, using too big a syringe can be prevented. According to some embodiments, the syringe size limitation is for syringes with size less then: 60, 50, 40, 30, 20, 10 ml. According to some embodiments, the user can grip the syringe and the gripping handle with the same hand.

According to some embodiments, the device includes a syringe seal mechanism. According to some embodiments, the syringe may be attached to the gripping handle or casing in a sealed manner According to some embodiments, the syringe may be releasably fitted into the gripping handle or casing. According to some embodiments, the gripping handle or casing may be fitted to one or more tubes that connect the Y or T connector to an exterior irrigation and or suction in a sealed manner (in the text it will be called syringe seal despite it possibly being other kinds of irrigation and aspiration sources).

According to some embodiments, the gripping handle or casing is fitted to house two syringes, a first syringe for irrigation and a second syringe for aspiration. According to some embodiments, the aspiration syringe is bigger than the irrigation syringe to provide the high negative pressure needed for viscus mucus suction without the risk of creating too high a pressure in the sinus. According to some embodiments, the syringes might have one direction flow valve, such as a duckbill valve. Such one-way valves are needed to prevent air and liquid flow from one syringe to the other and reduced affect in the sinus cavity. Yet according to additional embodiments, the flow into and out of the syringes can be controlled with a switch or a handle or a tap.

According to some embodiments, the gripping handle includes a mechanism that controls the syringe. According to some embodiments, pressing the gripping handle advances or retrieves the syringe piston while a first spring presses the piston to the other direction. According to some embodiments, upon pressing the gripping handle it returns into its original location by a second spring. According to some embodiments, the gripping handle may move the syringe piston with a ratchet mechanism, such as a linear ratchet.

According to some embodiments, the syringe piston is controlled by an actuator. According to some embodiments, the actuator is a motorized actuator. According to some embodiments, the actuator is a motorized syringe pump. According to some embodiments, the syringe pump is positioned in the device gripping handle or in the device casing. According to some embodiments, the syringe pump is positioned outside of the device gripping handle or in the device casing.

According to some embodiments, the cannula may be advanced and retrieved using a handle (cannula handle). According to some embodiments, the cannula handle is connected to the liquid tube. According to some embodiments, the cannula is located inside the device casing and the cannula handle outside of the device casing. According to some embodiments, the cannula handle slips over the device casing. According to some embodiments, the device casing has an open side tunnel According to some embodiments, at least one pin ribbon or screw is connecting the cannula handle to the cannula or liquid tube, and the pin ribbon or screw is movable back and forward within the tunnel.

According to some embodiments, the cannula handle enables one hand insertion and retrieval of the cannula. According to some embodiments, the user can grip the syringe, the gripping handle, and the cannula handle with the same hand. According to some embodiments, the cannula handle may be controlled using the user index finger of the same hand that holds the device. According to some embodiments, the cannula handle may be controlled using the user thumb of the same hand that holds the device. In some embodiments, the cannula handle has a lever that enables longer advancement of the cannula in relation to the cannula handle advancement. In other embodiments, the cannula advancement is linear to the cannula handle advancement. In some embodiments, the cannula and the cannula handle may both move together forward and backward along the same linear axis. According to some embodiments, the cannula may be advanced up to 10, 20, 30, 40, 50, 60 mm into the sinus. Each possibility represents a separate embodiment.

According to some embodiments, pressing the gripping handle advances or retrieves the cannula or the liquid tube. According to some embodiments, following the pressing of the gripping handle, a spring returns it to its original position. According to some embodiments, the gripping handle moves the cannula or the liquid tube with a ratchet mechanism, such as a linear ratchet.

According to some embodiments, the cannula may provide tactile feedback via the cannula handle when it is subject to resistance such as from a nasal mucosa, a infundibulum, a sinus ostia, or a sinus wall and sinus lower part. Such tactile feedback may assist the user to locate the cannula position in space and make decisions regarding the amount of force he may apply on the device and cannula handle. Therefore, the tactile feedback may prevent the user from harming and injuring the patient.

According to some embodiments, the device shall have visual marks that indicate the distance the cannula distal tip has advanced over the tubular member distal tip. Such visual feedback may assist the user to locate the cannula position in space and make decisions regarding the amount of force he may apply on the device and cannula handle. Therefore, the tactile feedback may prevent the user from harming and injuring the patient.

According to some embodiments, the cannula handle has a mechanism that locks it from advancing or retrieving. The mechanism may be released by pushing or moving a trigger. Such a trigger may prevent unintended cannula retrieval from the patient sinus. According to some embodiments, the trigger may be controlled with the same hand that is moving the cannula handle and holding the device. According to some embodiments, the trigger is positioned such that it may be pushed or moved by the same movement that advances or retrieves the cannula handle. According to some embodiments, the trigger is positioned such that it may be pushed or moved in the same direction as the cannula handle movement. According to some embodiments, the trigger is based on a spring or spring like mechanism. The spring may push or pull one or more protrusions fitted into one or more sockets. That way the trigger can prevent or allow movement of the cannula handle.

According to some embodiments, the locking mechanism such as the protrusions and sockets is not active during the initial advancement length. According to some embodiments, it is positioned only in the distal part of the device handle overlapping area. That way the friction of the initial cannula movement is reduced. According to some embodiments, the initial cannula advancement distance is less than 5, 10, 15, 20 mm (each possibility represents a separate embodiment). According to other embodiments the locking mechanism is based on friction.

According to some embodiments, the cannula handle is capable of rotating the cannula around its central axis in addition to back and forth movement. According to some embodiments, cannula handle rotational movement linearly rotates the cannula. According to some embodiments, cannula handle movement rotates the cannula using a lever or a gear. According to some embodiments, cannula handle movement may rotate the cannula using a string. According to some embodiments, the cannula handle may bend the cannula distal end using one or more strings. According to some embodiments, the cannula handle may pull a string that causes the cannula to bend in one direction and a spring to bend the cannula to the opposite direction. According to some embodiments, the strings are located outside of the cannula interior lumen. According to some embodiments, the strings are located in additional interior lumen or lumens. According to some embodiments, the same cannula handle controls at least: forward and backward movement and rotational movement and cannula distal end bending. According to some other embodiments, more than one cannula handle may control at least: forward and backward movement and rotational movement and cannula distal end bending.

According to some embodiments, the cannula handle has a mechanical connection to the liquid tube via an aperture in the device casing. According to some embodiments, the cannula handle has a magnetic connection to the liquid tube. The handle and or the liquid tube contain magnets and there is no need for an aperture in the device casing.

According to some embodiments, a rotating cannula handle may rotate the cannula around its axis. According to those embodiments, a rotating cannula handle is an additional handle to the cannula handle. According to some embodiments, the user may hold the device handle by one hand and rotate the cannula handle with the same hand. According to those embodiments, a rotating cannula handle may be used by the device user using a different finger than the finger he uses to advance and retrieve the cannula handle. According to those embodiments, the user may rotate the rotating cannula handle and to advance or retrieve the cannula handle simultaneously. According to some embodiments, he might do it using only one hand. According to some embodiments, a rotating cannula handle is or comprises a dial or a cannula dial.

According to some embodiments, the rotating cannula handle or dial is mechanically connected to the liquid tube, or to the cannula. Rotation of the dial, rotates the cannula around its axis. According to some embodiments, the cannula distal end is not straight. According to some embodiments, it comprises a curve. According to some embodiments, the cannula distal end has 10, 20, 30, 40 degrees bend, each possibility represents a separate embodiment. According to some embodiments, rotation of the dial, liquid tube and or cannula, may facilitate cannula insertion into a patient's sinus, by providing better orientation toward a sinus ostium.

According to some embodiments, the rotating cannula handle is directly connected to the cannula. According to some other embodiments, the rotating cannula handle is in-directly connected to the cannula. The indirect connection can include a gear, a lever, a bulge or a rod. According to some embodiments, the rotating cannula handle is located near the device handle and the connection between the rotating cannula handle to the cannula is located distally to the device's distal cannula seal. According to some embodiments, the dial rotating cannula handle or dial comprises a protrusion or a lever that connects it to the cannula over the device distal cannula seal. According to some embodiments, the connection between the rotating cannula handle to the cannula is linear. According to some embodiments, the connection between the rotating cannula handle to the cannula is not linear.

According to some embodiments, the connection apparatus between the rotating cannula handle and the cannula is located outside of the device casing. According to some embodiments, the connection apparatus is connected to the cannula distally to the device distal cannula seal. According to some embodiments, the connection apparatus between the rotating cannula handle and the cannula is located within the device casing. According to some embodiments, at least part of the rotating cannula handle or dial is located within the device casing. According to some embodiments, the device casing comprises one or two or more openings. The openings may enable the user to rotate the dial while the device casing distal part is connected to the device casing proximal part.

According to some embodiments, the liquid tube comprises one tube that connects the cannula and the T or Y connector. According to some embodiments, the liquid tube comprises more than one tube that connects the cannula and the T or Y connector. According to some embodiments, the liquid tubes are movable and at least one of them can be inserted into at least one other tube inner lumen in a telescopic manner. It is understood that during such movement the connection between the tubes remains to be sealed, such as by O-rings seals. The sealed telescopic tube mechanism might be beneficial in shortening the device length.

According to some embodiments, the device comprises a handle (wire handle) that advances and retrieves the rotating wire. According to some embodiments, the wire handle advances the wire transmission shaft. According to some embodiments, the wire transmission shaft and wire are located inside the device casing and the handle outside of the device casing. According to some embodiments, the outer wire handle and the inner wire transmission shaft are connected via an open tunnel in the device casing side (as the cannula handle). According to other embodiments, the connection is located on the proximal end of the device casing.

According to some embodiments, the wire handle might advance, retrieve or rotate the wire transmission shaft in comparison to the liquid tube and or the T or Y connector. According to some embodiments, the wire handle is positioned proximally to the liquid tube and or the T or Y connector. According to some embodiments, the wire handle is connected to a proximal part of the wire transmission shaft that protrudes out of the liquid tube and or the T or Y connector. According to some embodiments, the wire handle slips over the device casing proximal part. According to some embodiments, at least part of the handle slips inside the device casing proximal part. According to some embodiments, the wire handle and the device casing contain rails that prevents the handle rotation relative to the device casing. According to some embodiments, the wire handle and/or the device casing contain a stopper mechanism such as pins that prevent the handle from separating from the device casing. According to some embodiments, the wire handle has a magnetic connection to the wire transmission shaft. According to some embodiments, the wire handle is connected to the wire transmission shaft via an aperture in the liquid tube side wall. The aperture in the liquid tube is sealed by a seal, around the handle. According to some embodiments, the seal in the liquid tube is movable, collapsible or stretchable. According to some embodiments, the seal is not movable, and the wire handle uses a gear in order to advance and retrieve the wire transmission shaft. According to some embodiments, the wire handle and the wire transmission shaft contain a magnetic connection and there is no need for an aperture in the device casing or in the liquid tube or the need to position the wire handle in the device proximal part.

According to some embodiments, the wire handle advances and retrieves the wire transmission shaft and the rotating wire within the cannula and out of the cannula. According to some embodiments, the wire handle advances and retrieves the wire transmission shaft and the rotating wire within the tubular guide and out of the tubular guide.

In some embodiments, the wire handle has a lever that enables longer advancement of the wire in relation to the handle advancement. In other embodiments, the wire advancement is linear to the handle advancement. In some embodiments, the wire and the handle are both moving together forward and backward along the same linear axis. According to some embodiments, the device shall have visual marks that indicate the distance the wire distal tip has advanced. Such visual feedback may assist the user to locate the wire position in space in relation to the sinus and the cannula. According to some embodiments, the wire may be advanced up to 10, 20, 30, 40, 50, 60, 70 mm into the sinus (each possibility represents a separate embodiment).

According to some embodiments, the device has a mechanism that moves one of the wire or cannula handles in the same direction as the other handle, as a result of the other handle's movement. According to some embodiments, the movement is partial. According to some embodiments, moving the cannula/liquid tube forward advances the wire in the same direction. According to some embodiments, the movement starts only after the cannula has been advanced over a certain point. According to some embodiments, the certain point distance is less than 10, 20, 30, 40, 50 mm (each possibility represents a separate embodiment). According to some embodiments, both handles are connected. According to some embodiments, the liquid tube and the wire transmission may be connected during advancement/retrieval. According to some embodiments, the connection may be by a bump or a pin, that drags the other part as it moves in a certain direction.

According to some embodiments, the liquid tube contains at least part of the wire transmission shaft that is connected to the wire. According to some embodiments, the liquid tube or the wire transmission has one or more bumps that prevent the wire transmission shaft distal end from entering into the cannula and or being proximate to the cannula proximal end. That way the bump prevents the wire transmission shaft from partial or full occlusion of the device.

According to some embodiments, the connection between the liquid tube and the wire transmission shaft is sealed by the movable seal (which can also be referred to as the cannula seal). According to some embodiments, the movable seal is surrounding part of the wire transmission shaft and is contained within part of the liquid tube. According to some embodiments, the movable seal has a toroid shape. According to some embodiments, the seal can move forward and backward. According to some embodiments, the seal is connected or partially connected to the cannula handle for at least part of it path. According to some embodiments, the cannula handle movement can linearly progress the seal for at least part of it path. According to some embodiments, the seal comprises one or more O-rings. According to some embodiments, the seal movement can press the liquids within the liquid tube toward the Y or T connector and toward the syringe or motorized suction irrigation machine. The pressing ability is beneficial in collecting mucus from within the device, such as for lab analysis. Without the ability to press the mucus out of the device, a bigger part of the mucus might get lost. An additional attribute of the movable seal is that it enables to shorten the device length.

According to some embodiments, the movable seal does not undesirably move forward and backward because of the irrigation and aspiration liquids pressures, due to the cannula handle locking mechanism. The cannula handle locking mechanism locks the cannula, unless the user presses the cannula handle. Otherwise irrigation and aspiration liquid pressure changes could force the cannula out of the patient's sinus.

According to some embodiments, the device has an additional proximal seal (motor seal). The proximal seal seals the connection between the Y or T connector and the motor. The proximal seal is crucial for simultaneously rotating the wire and irrigation or aspiration of the sinus cavity. Simultaneously rotating the wire and irrigation or aspiration is needed for creating the liquids shear forces that clean the mucus out of the sinus cavity areas without direct contact with the grinding wire. Additionally, simultaneously rotating the wire and aspiration is needed for preventing cannula/liquid tube occlusion. Occlusion may occur due to the mucus sticky nature and the mucus ability to restore its viscosity after tearing apart within seconds.

According to some embodiments, the proximal seal is a magnetic seal. Rotation of a proximal/exterior magnet connected to the motor is rotating additional distal/interior magnet within the proximal end of the Y or T connector. The additional magnet is connected to the wire transmission shaft. Between the magnets, there is a sealed wall. According to some embodiments, the magnets or the wire transmission shaft may contain a bearing mechanism in order to reduce the friction.

According to some embodiments, the proximal seal is surrounding the wire transmission shaft that connects the wire to the motor. According to some embodiments, the proximal seal is affixed to the device casing and the transmission shaft is rotating within the seal. According to some embodiments, the transmission shaft can be linearly advanced and retrieved within the seal. According to some embodiments, the transmission shaft can be advanced and retrieved within the seal by the wire handle while the motor is rotating the transmission shaft. According to some embodiments, the seal is made of one or more O-rings. According to some embodiments, the O-rings are pressing the inner transmission shaft. According to some embodiments, the O-rings are being pressed by its surrounding cavity. According to some embodiments, the O-rings are pressed from its surrounding cavity and pressing the transmission shaft simultaneously. According to some embodiments, the O-rings are surrounded and pressed by additional O-rings. According to some embodiments, one of the O-rings is softer than the other. According to some embodiments, the seal is lubricated with oil or grease such as silicone oil or silicone grease. According to some embodiments, the seal contains a reservoir of lubrication materials.

According to some embodiments, the proximal seal is a sliding/contact/plain—bearing. According to some embodiments, the proximal seal bearing is comprised of a stator and a rotor. According to some embodiments, one of the stator and a rotor may be made of metal such as steel and the other one may be made of silicon or plastic such as Teflon. According to some embodiments, the non-metallic part can be flexible and press the metallic part. According to some embodiments, the connection between the bearing sides is the connection between the reusable motor and the disposable distal tip. According to dose embodiments the bearing sides connect with a fast connection mechanism such as a click or a snap.

According to some embodiments, the proximal seal is a Labyrinth seal. One side of the labyrinth seal is connected to the engine and the other one is connected to the transmission shaft or to the rotating wire. According to some embodiments, the labyrinth seal contains within it soft or expandable parts or springs that improve the contact between the Labyrinth seal stator and rotor. According to some embodiments, the labyrinth seal contains within it a lubrication or sealing medium such as oil or grease.

According to some embodiments, the device has a sealed cavity formed between the syringe/suction/irrigation machine, the proximal seal (connection with the motor), the liquid tube and the cannula, with an opening only at the distal part of the cannula. According to some embodiments, the sealed cavity remains sealed during one or more of the following: syringe piston movement, suction, irrigation, motor rotating of the wire transmission shaft and the wire, cannula and or liquid tube advancement or retrieval, wire and wire transmission shaft advancement or retrieval. The opening of the sealed cavity is only at the distal part of the cannula. According to some embodiments, the sealed cavity remains sealed due to the simultaneous action of the cannula seal, the proximal seal, and the syringe seal. The sealed cavity that remains sealed during the device parts insertion into the sinus and during device activity is crucial for its ability to provide efficient sinus lavage.

According to some embodiments, the guiding tube or the tubular member is directly connected to the device casing. According to other embodiments, the guiding tube or the tubular member is connected to the device casing with a tubular member connector.

According to some embodiments, the tubular member connector may enable the user to change the tubular member orientation and rotate it. According to some embodiments, the tubular member connector may enable the user to replace the guiding tube. According to some embodiments, the tubular member connector connects the cannula by a snap or threading mechanism such as a luer. According to some embodiments, the guiding tube luer is a locking luer. According to some embodiments, the locking luer threading nut is capable of locking the guiding tube in every orientation. The threading nut rotates and threads itself on the stationary guiding tube. That way the user might change the guiding tube orientation and/or replace the guiding tube at will.

According to some embodiments, the guiding tube, or at least part of it, is bendable. According to some embodiments, the guiding tube may be bent by the device user to fit to the shape of a creation sinus ostia or other nasal structure, or to facilitate ostial penetration. According to some embodiments, the device kit may be comprised of a guiding tube bender, that may be used to bend the guiding tube to desired shapes. According to some embodiments, the guiding tubes might be bent to angles of 110-90 for the maxillary sinus, 0-30 for the sphenoid sinus, 60-80 for the frontal sinus, 30-70 for the Eustachian tubes.

According to some embodiments, the device kit might contain more than one guiding tube with different angles intended for different sinuses, such as the maxillary sinus, frontal sinus, sphenoid sinus, the middle ear via the Eustachian tube. According to some embodiments, the guiding tubes might have angles of 110-90 for the maxillary sinus, 0-30 for the sphenoid sinus, 60-80 for the frontal sinus, 30-70 for the Eustachian tubes.

According to some other embodiments, the guiding tube can be bent. According to some other embodiments, the guiding tube can be bent so the distal end of the tube may face at least one of the nasal cavities openings. According to some other embodiments, the guiding tube can be bent with a controlling handle. According to some other embodiments, the guiding tube can be bent by the device user using his/hers hands or using a bending device or a jig. According to some embodiments, the guiding tube can have bending angles of 110-90 for the maxillary sinus, 0-30 for the sphenoid sinus, 60-80 for the frontal sinus, 30-70 for the Eustachian tubes.

According to some other embodiments, the guiding tube can be bent. According to some other embodiments, the guiding tube can be bent so the distal end of the tube may face at least one of the nasal cavities openings. According to some other embodiments, the guiding tube can be bent with a controlling handle. According to some other embodiments, the guiding tube can be bent by the device user using his/hers hands or using a bending device or a jig. According to some embodiments, the guiding tube can have bending angles of 110-90 for the maxillary sinus, 0-30 for the sphenoid sinus, 60-80 for the frontal sinus, 30-70 for the Eustachian tubes.

According to some embodiments, the guiding tube is suitable to contain one cannula. According to some other embodiments, the guiding tube is suitable to contain more than one cannula. According to some other embodiments, the guiding tube is suitable to contain one or more devices. The device has a proximal and distal end. It can be advanced forward and backwards. It can be advanced over the guiding tube distal end.

According to some other embodiments, the guiding tube distal end has a cut conic shape within its interior lumen. That shape can enable only one cannula or one device to protrude out of the guiding tube distal end. Additionally, that shape will center the cannula or device on the guiding tube central axis. According to some embodiments, the cannulas or the devices might be connected to the guiding tube with a spring. The spring is configured to retract the cannula or device that protrudes out of the guiding tube distal end. A pin, a handle, or other mechanism might be used to resist the spring. According to some embodiments, advancement of one cannula or device while another cannula or device is located in the guiding tube distal end, will activate the retracting spring of the cannula or device that is located in the guiding tube distal end.

According to some embodiments, the device can be an additional therapeutic and diagnostic instrument such as, guidewire, light-wire for trans-illumination, optic fiber for visualization or recording, optic fiber for pathogen eradication, swab, cutting device, balloon, dilatation device, vibrating piezoelectric crystal, laser or heat source, absorbable material soaked with drug, all the above are separate embodiments.

According to some embodiments, the device can be a piston that can push or suck a material. According to some embodiments, the piston can push a drug into the sinus. According to some embodiments, the drug can be a non-liquid state such as gel, foam or solid state. According to some embodiments, the piston can push a drug via the guiding tube conic distal end into a sinus cavity. According to some embodiments, the guiding tube may be comprised of an exterior mechanism that seals the sinus ostium opening, such as a foam ring that surrounds the guiding tube.

According to some embodiments, the removable connector may be comprised of a T or a Y connector. The connector may contain a locking luer. According to some embodiments, the locking luer threading nut is capable of locking the guiding tube in every orientation. The threading nut rotates and threads itself on the stationary guiding tube. According to other embodiments, the guiding tube may have an additional side tube on its side, creating an interior lumen of Y or T shape.

According to some embodiments, the additional tube of the connector or guiding tube may be fitted for suction, such as a connection to a suction machine. Additionally, according to some embodiments, the proximal part of the guiding tube may be sealed around the cannula. According to some embodiments, such seal is comprised of one or more O-rings. Additionally, according to some embodiments, the seal is located around the cannula or around the liquid tube in the guiding tube connector or in the device casing. The seal enables the cannula movement forward and backward with minimal friction. That way the device might prevent or at least reduce liquid flow from the irrigated sinus to the nasal cavity. Those liquid are a major discomfort for the patients, especially with the bitter taste of local anesthesia. In other cases, therapeutic drugs, pathogens or bacteria may be suctioned, instead of flowing into the nasal cavity, throat or lungs.

According to some embodiments, the additional tube of the connector or guiding tube may be fitted for guidewire insertion. According to some embodiments, the guidewire is a light wire. Such light wire may assist the user by transillumination of the sinus in order to verify the sinus actual location. According to some embodiments, the additional tube of the connector or guiding tube may be fitted for irrigation as well as suction. According to some embodiments, the additional tube of the connector or guiding tube may be fitted for additional therapeutic and diagnostic instruments, such as optic fiber for visualization, swab, cutting device, balloon, dilatation device or a grasper.

According to some embodiments, the guiding tube or the tubular member has an atraumatic distal end. According to some embodiments, the atraumatic distal end is smooth. According to some embodiments, the tubular member distal end is soft or collapsible. According to some embodiments, the tubular member distal end has a circumstancing ring of soft or collapsible material, such as foam. According to some embodiments, the ring of soft or collapsible material can seal the sinus opening. According to some embodiments, the ring can prevent irrigation liquids from flowing into the nasal cavity. According to some embodiments, the distal tip of the guiding tube may include therein or mounted thereon, visualization equipment such as a camera, a lens, a light source or a combination thereof. According to some embodiments, the distal tip of the guiding tube may include therein or mounted thereon, an attachment mechanism for visualization means such as an endoscope. Such visualization equipment can assist the user to see the sinus opening and facilitate cannula insertion. According to some embodiments, the device motor is connected or has a connector to the device casing. According to some embodiments, the device motor is at least partially located within the wire handle. According to some embodiments, the connection enables fast connection and removal of the motor from the device. According to some embodiments, the device casing fully or partially surrounds the device motor. According to some embodiments, the motor is connected to the device casing or wire handle from its side. According to some embodiments, the motor is connected to the device casing wire handle from its proximal end. According to some embodiments, the device casing has a mechanism that prevents the motor from falling off. According to some embodiments, the mechanism is an O-ring. According to other embodiments it is a snap connector. According to some embodiments, it is a handle. According to some embodiments, a spring fixes the motor handle in a position that prevents the motor from disconnecting the device. Pressing the motor handle against the spring enables motor disconnecting.

According to some embodiments, the motor is an electric motor. According to some embodiments, the motor is configured to rotate the transmission shaft and or rotating wire. According to some embodiments, the motor is configured to advance and retrieve the transmission shaft and or rotating wire along a logistical axis. According to some embodiments, the motor is a piezoelectric crystal that vibrates the transmission shaft and or rotating wire. According to some embodiments, the vibration is ultrasonic. According to some embodiments, the motor or piezoelectric crystal is configured to vibrate the device cannula. According to some embodiments, the motor or piezoelectric crystal is configured to vibrate the device cannula. According to some embodiments, the motor or piezoelectric crystal is configured to vibrate the device guiding tube or bent shaft. According to some embodiments, the vibration is configured to vibrate the mucus. According to some embodiments, the vibration is configured to vibrate the nasal and sinus mucosa. According to some embodiments, the vibration is configured to vibrate the sinus ostial mucosa. Vibration of thickened nasal or sinus mucosa can reduce its liquid content, and shrink its size without harming it. It can be beneficial in restoring mucosal clearance, opening mucosal occlusions, and airing the sinuses.

According to some embodiments, the flexible hollow cannula includes an aperture in its side wall at a distal end thereof, such that the flexible grinding wire may exit the flexible hollow cannula through the aperture. It is understood that such configuration may enable sealing of the distal end of the hollow cannula with an atraumatic tip. According to some embodiments, the atraumatic tip may include a taper that directs the wire towards the side aperture. It is further understood that by exiting the hollow cannula through the aperture, the grinding wire may be directed away from sensitive areas where it could potentially cause harm. According to some embodiments, the cannula side aperture is configured to direct the flexible grinding wire toward a desired location, such as towards a polyp or polypoid tissue. According to some embodiments, the cannula can be advanced, retrieved and rotated in order to position the side aperture in front of or away from a desired location. According to some embodiments, the cannula aperture is positioned towards the sphenoid sinus dorsal or medial wall, and away from possible blood vessel in the sinus. According to some embodiments, the cannula aperture is positioned towards the maxillary sinus dorsal or medial wall, and away from the eye. According to some embodiments, the cannula can have more than one aperture on its distal end. According to some embodiments, the cannula apertures may be round or elliptic.

According to some embodiments, the grinding wire may be configured to prevent, loosen and/or remove mucus material accumulating and/or clogging the hollow cannula. According to some embodiments, the grinding wire may be configured to scrape, loosen and/or remove material sticking to the walls of the sinus cavity. According to some embodiments, the flexible grinding wire may have an external diameter of 0.5 mm or below, 0.4 mm or below, 0.3 mm or below, 0.24 mm, 0.2 mm or below or 0.1 mm or below. Each possibility is separate embodiment. According to some embodiments, the wire is made of more than two strings each having an external diameter of 0.5 mm 0.1 mm or below, 0.08 mm or below, 0.05 mm or below. Each possibility is a separate embodiment. According to some embodiments, the flexible grinding wire may include a super-elastic material. According to some embodiments, the super-elastic material may be a pseudo-elastic material. According to some embodiments, the super-elastic material may be a Nickel-Titanium alloy.

According to some embodiments, the wire is comprised of more than one material and or structure. According to some embodiments, the wire is comprised of a distal part and a proximal part. According to some embodiments, the distal part is more flexible. For example, according to some embodiments, the wire is made of a nitinol wire in its proximal end and nitinol cable loop or L in its distal end. The nitinol wire can transmit the torque in the bent cannula or guiding tube, and the nitinol cable loop or L shape stirs the liquids in the sinus without harming the mucosa. According to some embodiments, a crimped metal tube connects the wire distal and proximal parts. According to some embodiments, a plastic tube connects the wire distal and proximal parts. According to some embodiments, the tube is a heat shrink plastic tube. According to some embodiments, the wire is comprised of a plastic optic fiber capable of bending and of transmitting light.

According to some embodiments, the device comprises a non-linear shape of the grinding wire distal end to facilitate liquids stirring and mucus grinding. For example, rotation of wires with L or J distal shapes creates higher liquid movement than rotation of a straight wire. Rotation of a loop was empirically found to create significantly higher effect on mucus grinding in comparison to curved distal shapes. According to some embodiments, the device comprises a loop in the grinding wire distal end to facilitate liquid stirring and mucus grinding.

According to some embodiments, a cable such as a steel or nitinol cable transmits the transmission between the transmission shaft and the wire distal end. According to some embodiments, the wire diameter is equal or less than about 0.8 mm, 0.6 mm, 0.4 mm, 0.35 mm, 0.3 mm, 0.24 mm, 0.2 mm, each possibility represents a separate embodiment. According to some embodiments, the wire distal end comprises a nitinol loop. According to some embodiments, the loop diameter is equal or less than 3 cm, 2 cm, 1 cm, 5 mm According to some embodiments, a metal crimp connects the cable and the nitinol wire loop. According to some embodiments, the nitinol loop is a symmetric loop. According to some embodiments, the nitinol loop is not a symmetric loop. According to some embodiments, the nitinol loop can be advanced and retrieved out of and into the cannula distal end or cannula side opening. According to other embodiments, the nitinol loop can be partially inserted into the cannula distal end. According to some embodiments, the nitinol loop shape enables the loop proximal part to be inserted into the cannula distal end but the distal part of side nitinol loop cannot be inserted into the cannula distal opening. According to some embodiments, the nitinol loop shape has curves, protrusions or kinks that prevent it from full insertion into the cannula distal end. According to some embodiments, the nitinol loop distal end size, while partially being inserted into the cannula, is equal or less than 3 mm, 2 mm, 1 mm, 0.8 mm, 0.5 mm, each possibility represents a separate embodiment. According to some embodiments, the nitinol loop comprises more than one wire, for example, it can be comprised of two or more loops, or it can be comprised of tree wires. In those embodiments the nitinol loop may have a 3D cage shape.

According to some embodiments, the nitinol loop, when it is mounted on the cannula distal end, may be inserted into a patient's sinus opening with the cannula. According to some embodiments, the nitinol loop is being used as an atraumatic cannula tip. According to some embodiments, advancement of the cannula handle forward advances the cannula and the nitinol loop forward, such as into a sinus opening. According to some embodiments, advancement of the wire handle advances the wire and the nitinol loop out of the cannula. According to some embodiments, advancement of the wire and the nitinol loop out of the cannula distal end enables the nitinol loop to assume its original shape. According to some embodiments, retrieving of the wire and the nitinol loop into the cannula distal end reduces the loop distal end size. According to some embodiments, the user can rotate the distal nitinol loop orientation by rotating the motor. According to some embodiments, the rotation may facilitate cannula insertion into the sinus ostium, for example by better fitting to the ostium orifice shape.

According to some embodiments, the nitinol loop lateral sides are symmetrical. According to some embodiments, the nitinol loop lateral sides are not symmetrical, and the nitinol loop has offsite angle. According to some embodiments, the nitinol loop angle is equal or less than about 60, 40, 30, 20, 10 degrees, each possibility represents a separate embodiment. According to some embodiments, the user can rotate the distal bent nitinol loop by rotating the motor, while pushing and pulling the cannula handle back and forth. According to some embodiments, the angle may facilitate cannula insertion into the sinus ostium, for example, by more easily finding the sinus ostium, or by better cannula distal end alignment with the sinus ostium.

According to some embodiments, the user may insert the cannula and the nitinol loop into a patient's sinus within a guiding tube and using the cannula handle, advance the nitinol loop deeper into a patient's sinus using the wire handle, the loop assumes its pre-shaped structure, the user may rotate the loop using the motor, irrigate and aspirate the sinus via the cannula into a syringe, while the loop is rotating, retrieve the nitinol loop proximal end into the cannula and remove the cannula.

According to some embodiments, at least part of the wire is a composite material with metallic core, such as a nitinol rope, and exterior plastic cover. According to some embodiments, the plastic covering is stiffer than the inner core. According to some embodiments, the plastic covering has better pushability capability than the flexible metal core, so it will not get entangled around itself while it is advanced forward. According to some embodiments, the plastic covering reduces interior wire wear and tear during high RPM rotation. According to some embodiments, the plastic covering prevents the metal strings from move away from each other. According to some embodiments, the plastic covering is a heat shrink. According to some embodiments, the plastic cover may have a wall size of 0.1 mm or below, 0.5 mm or below, 0.01 mm or below, 0.05 mm or below or 0.01 mm or below. Each possibility is a separate embodiment.

According to some embodiments, the distal end of the flexible hollow cannula comprises an atraumatic tip. According to some embodiments, the distal end of the flexible hollow cannula or the atraumatic tip comprises a therapeutic or diagnostic device. According to some embodiments, such therapeutic or diagnostic device may be operated during sinus irrigation and or aspiration and or during wire rotation. According to some embodiments, the therapeutic or diagnostic device may be operated before or after sinus irrigation and or aspiration without removing the flexible hollow cannula distal tip out of the patient's sinus ostium. According to some embodiments, the therapeutic or diagnostic device may be operated before or after sinus irrigation and or aspiration without removing the hollow shaft distal tip out of it location in the nose: facing the patient's sinus ostium.

According to some embodiments, the therapeutic or diagnostic device is located in the hollow shaft distal end. According to some embodiments, the therapeutic or diagnostic device is located in the hollow shaft distal end and it may be operated during sinus irrigation and or aspiration and or during wire rotation. According to some embodiments, the therapeutic or diagnostic device may be operated before or after sinus irrigation and or aspiration without removing the hollow shaft distal tip out of the patient sinus ostium.

According to some embodiments, the therapeutic or diagnostic device may contain an optic fiber, electric wire, a lens, a light source such as LED, or any combination thereof. Sinus transamination may help the user to verify the distal tip location within the sinus. According to some embodiments, a laser may be used to take sinus dimensions and improve device orientation within the sinus. Sinus illumination may also provide therapeutic value by removing bacteria from the sinus mucosa. According to some embodiments, the device's distal tip may emits light by a light source or may transmit light into the sinus. According to some embodiments, the light destroy or damage at least some of the bacteria in the sinus. According to some embodiments, the light may be ultraviolet or blue light such as: 250-270 nm, 200-280 nm ultraviolet A, B or C irradiation, 402-420 nm, 400-470. According to some embodiments, the light may provide photodynamic therapy in which the light illuminates a photosensitizer such as methylene blue, and the photosensitizer harms bacteria in the sinus. Other photosensitizers may include Allumera, Photofrin, Visudyne, Levulan, Foscan, Metvix, Hexvix, Cysview and Laserphyrin, with others in development, e.g. Antrin, Photochlor, Photosens, Photrex, Lumacan, Cevira, Visonac, BF-200 ALA, Amphinex and Azadipyrromethenes.

According to some embodiments, the light may be diffused by the stirring liquids in the sinus cavity. According to some embodiments, the stirring wire stirs the liquids in the sinus cavity and the liquids diffuse the light over the sinus walls.

According to some embodiments, the light and the optic fiber are capable of detecting Oxidative Stress. According to some embodiments, the light and the optic fiber are configured to detect the structure, size and density of blood vessels in the mucosa. According to some embodiments, the light green such as around 605 nm or around NIR 830. According to other embodiment the light and the optic fiber uses laser Doppler to detect structure, size and density of blood vessels in the mucosa. Structure, size and density of blood vessels may assist in determining the mucosal disease severity. Inflammation cases increased blood flow to the mucosa. Determining the mucosal disease severity might affect the user decisions regarding the optimal course of treatment. For example, blood vessel increased size and density might imply that the patient has chronic disease and it might require corticosteroids or surgical solution. According to some embodiments, the user can use the light to detect the hyper-vascular/inflamed mucosa focal location in relation to the sinus/nasal map.

According to some embodiments, the liquids stirring by the wire during illumination may act as a lens and enable illumination of more extensive parts of the sinus wall than illumination without liquid stirring.

According to some embodiments, the therapeutic or diagnostic device may contain camera, lens, optic fiber that enable taking pictures or video from the sinus internal cavity, or any combination thereof. Imaging of the sinus internal cavity may enable the user to verify the device location within the sinus, to locate the device in optimal position, to make decisions on the most appropriate treatment options, to make a decision for how long the sinus irrigation should continue and provide visual feedback if the treatment was successfully completed. According to some embodiments, the pictures are video pictures. According to some embodiments, the device contains separate optic fibers for illumination and for taking pictures. According to some embodiments, the device comprises a screen or a connection to a screen. According to some embodiments, the cannula may include on a distal tip thereof, visualization equipment (such as a camera) that may be directed towards the rotating wire, and may provide pictures of the rotating wire.

According to some embodiments, the therapeutic or diagnostic device may contain an ultrasonic imaging mechanism. According to some embodiments, the therapeutic or diagnostic device may contain an ultrasonic mark such as a sound opaque mark or sonic beacon to be used with an exterior ultrasound device. According to some embodiments, the mark may enable the user to verify the device location within the nasal cavity. According to some embodiments, the therapeutic or diagnostic device may contain a radio mark such as a radio opaque mark or radio beacon to be used with an exterior radio device. According to some embodiments, the mark may enable the user to verify the device location within the nasal cavity. According to some embodiments, the device can comprise a magnetic mark and a magnetic exterior device for the same purposes. According to some embodiments, the device can comprise a light or radiation emitting mark, and an exterior light or radiation sensing device for the same purposes. According to some embodiments, the therapeutic or diagnostic device may contain a thermal beacon, such as LED (Light-emitting diode) to be used with an exterior thermal imaging device. According to some embodiments, the thermal beacon may enable the user to verify the device location within the nasal cavity. According to some embodiments, the exterior thermal imaging device is a thermal camera suitable to be used with a mobile device such as a cellphone or a tablet.

Some embodiments describe a method in which the user may use a thermal imaging device on a patient's sinuses to sense if the sinus area is hotter than its environment. According to some embodiments, the thermal imaging device is a thermal camera suitable to be used with a mobile device such as a cellphone or a tablet. The user may then insert into the patient's nasal cavity or sinus a guidewire/light wire/curved shaft/balloon dilation device, containing a thermal source such as LED in its distal end. The user may then verify the thermal source location in the nasal cavity using the thermal imaging device. Alternatively, the user may follow the thermal source movement in the nasal cavity using the thermal imaging device. The user may then preform surgical intervention in the nasal cavity or the sinus such as sinus ostial balloon dilatation or biopsy. The user may then lavage the nasal cavity or the sinus cavity. The user may then use the thermal imaging device to see that the temperature in the sinus was reduced by the lavage (immediately or in additional doctor visits). Each step may constitute separate embodiments.

According to some embodiments, the therapeutic or diagnostic device may contain a pressure sensor or a strain gauge. The pressure sensor or a strain gauge may be used to measure the pressure within the sinus, to avoid excess pressure, pain and injury, or to identify the device tip location in relation to the sinus wall and avoid excess pressure on the sinus mucosal wall or bottom, pain and injury, or to measure the sinus ostium diameter in order to provide the user better clinical understanding to assess the next surgical steps, such as ostial dilatation.

According to some embodiments, the therapeutic or diagnostic device may contain a lab on a chip, to analyze pathogens in the sinus. According to some embodiments, the lab on a chip may enable diagnosis of certain pathogens such as *Staphylococcus Aureus*. According to some embodiments, the lab on a chip may enable analysis of antibiotic resistance and enhanced diagnosis of certain pathogens such as Methicillin-Resistant *Staphylococcus Aureus*. According to some embodiments, the lab on a chip may enable analysis of the bacterial diversity of commensal sinus bacteria or the presence of probiotic bacteria species.

According to some embodiments, the therapeutic or diagnostic device may measure: c-reactive protein measurement and or Erythrocyte sedimentation rate apparatus such as CRP or ERS strips, White Blood Cells—WBC/Leucocytes indication for contamination, Neutrophils—NEUT indication for contamination, Lymphocytes—LYMPH/LYM indication for viral contamination, Monocytes—MONO indication for viral contamination, Basophils—BASO, Eosinophils—EOSIN/EOS indication for allergy, PHlevel, Nitric oxide NO or Nitrogen Dioxide NO2, a2-macroglobulin (as a marker for plasma contamination) lactoferrin (as a marker for glandular secretion), lactate dehydrogenase (as a marker for tissue injury), interleukin (IL)-1b, IL-8, tumour necrosis factor-a, eosinophil cationic protein and tryptase (as indicators for tissue inflammation), bacterial or other pathogens DNA sequencing, each option provides a separate embodiment.

According to some embodiments, the therapeutic or diagnostic device may comprise a Radar. According to some embodiments, the Radar may enable the user to map the sinus dimension and assist in locating the device's distal tip in the sinus space. According to some embodiments, the Radar may enable the user to detect substructures in the sinus such as Tumors, Lesions, Polyps Nerves, Mucoceles, fungal ball and mucus deposits. According to some embodiments, the Radar may enable the user to position the rotating wire in a harmless location, such as to avoid nerves in the sphenoid sinus, or in a therapeutic location, such as in the center of a fungal ball or mucus deposits.

According to some embodiments, the therapeutic or diagnostic device may comprise an electric wire, to sense the presence and location of nerves in the sinus by the nerves electric pulse. The device might also comprise a Voltmeter and Ampere meter. For example, that way the user might not harm the infraorbital nerve during maxillary sinus puncturing.

According to some embodiments, the therapeutic or diagnostic device may comprise a solid state LIDAR (Light Detection And Ranging). According to some embodiments, the LIDAR can be used to map the nasal and sinuses cavities. According to some embodiments, the LIDAR may be used to navigate the device in the nasal and sinuses cavities.

According to some embodiments, the therapeutic or diagnostic device may measure the sinus content resonance frequency. According to some embodiments, the resonance frequency measurement may identify the microbes and bacteria in the sinus.

According to some embodiments, the therapeutic or diagnostic device may comprise a grasper or, biopsy punch or other cutting device. Such a device might enable mucosa or polyps samples to be taken for lab analysis.

According to some embodiments, the therapeutic or diagnostic device may comprise a guidewire structure to assist the sinus penetration. According to some embodiments, the guidewire structure may have a hydrophilic cover. According to some embodiments, the guidewire structure may be lubricated.

According to some embodiments, the therapeutic or diagnostic device may comprise a piezoelectric crystal and electric wiring. According to some embodiments, the piezoelectric crystal vibration can be used to assist sinus lavage in mucus softening, or in reducing the viscosity of the mucus, or by breaking mucus deposits, or by moving/stirring the lavage liquids. According to some embodiments, the vibration can be ultrasonic and it can be mediated via the lavage liquids. According to some additional embodiments the piezoelectric crystal vibration can be used to expand the sinus ostial diameter. The vibration may remove part of the liquids in the ostial mucosa, and expand ostial size.

According to some embodiments, the therapeutic or diagnostic device may comprise a laser or heat source such as a monopolar for diathermy. According to some embodiments, it can be used for ablation of mucosa, such as polyps. According to some embodiments, it can be used to stop bleeding. According to some embodiments, the heat source is configured to heat the sinus liquids or the irrigation liquids. According to some embodiments, the heat source is configured to heat the sinus liquids or the irrigation liquids to more than about 20, 25, 30, 35, 37, 40° C., each possibility represents a separate embodiment. According to some embodiments, heating can improve the patient's experience and reduce discomfort. According to some embodiments, heating can improve the mucus dissolvent speed. According to some embodiments, the therapeutic or diagnostic device can comprise a thermometer. According to some embodiments, the thermometer may be used to verify that the device does not cause overheating of the tissue. According to some embodiments, the heat source and or thermometer may be located in the device syringe, within, around or near the liquid tube or the cannula coiling/braiding.

According to some embodiments, the therapeutic or diagnostic device may comprise an absorbable material such as a gel, foam, a pad or a sponge. According to some embodiments, the absorbable material may be used by the user to stop bleeding. According to some embodiments, the absorbable material may be filled with a drug. According to some embodiments, the drug is a mucolytic, an anesthetic drug such as lidocaine or cocaine, a decongestant drug such as epinephrine, an antibacterial drug, an inflammatory drug, steroids, such as corticosteroids or a combination of the above-mentioned drugs, each possibility/combination represents a separate embodiment. According to some embodiments, the drug can be eluted by pressing the absorbable material against the mucosa. According to some embodiments, the drug can be eluted by the irrigation liquids. According to some embodiments, the drug can be eluted in the medial meatus. According to some embodiments, the drug can be eluted in the sinus ostia. According to some embodiments, the drug can be eluted in the sinus cavity. According to some embodiments, the drug eluting absorbable material can be left within the sinus. According to some embodiments, the drug eluting absorbable material can be released from the device by liquid pressure. According to some embodiments, the drug eluting absorbable material can elute the drug over a period of more than 1 day, more than 1 week, more than 1 month, more than 3 months, more than 6 months, more than 12 months, each option represents a separate embodiment.

According to some embodiments, the therapeutic or diagnostic device may comprise an expandable mechanism such as a balloon. According to some embodiments, the balloon backbiter or punch may be used to expand the sinus ostia. According to some embodiments, the balloon may be used to measure the sinus ostial size. According to some embodiments, the user can inflate the balloon to a certain size and then pull it out of the sinus. This may provide the user an indication of the sinus ostial size.

According to some embodiments, the therapeutic or diagnostic device may electrify the liquids in the sinus. According to some embodiments, the rotating wire or other wire can electrify the liquids in the sinus. According to some embodiments, the cannula can electrify the liquids in the sinus.

According to some embodiments, all the above mentioned therapeutic or diagnostic devices may be inserted into the sinus via the guiding tube.

According to some embodiments, a sinus/ear opening dilation apparatus such as a balloon may be mounted over the cannula. According to some embodiments, such dilation apparatus may be configured to dilate a sinus opening or Eustachian tube. According to some embodiments, such dilation apparatus may be configured to dilate a sinus opening or Eustachian tube while the wire is rotating within the sinus/ear cavity. According to some embodiments, such dilation apparatus may be configured to dilate a sinus opening or Eustachian tube to facilitate the entry into a sinus cavity and/or sinus cleaning.

According to some embodiments, the syringe or the actuator or a device part that is connected to the syringe may have a pressure measurement mechanism. According to some embodiments, the pressure measurement mechanism may give the user indication regarding the pressure in the syringe or in the device or in the sinus, each possibility represents a separate embodiment. According to additional embodiments, the pressure measurement mechanism may give an indication of creation pressure threshold. According to additional embodiments, the device can be configured to stop pressure increment or reduce the pressure over creation pressure threshold. According to some embodiments, a valve, such as a spring based valve may reduce the pressure. According to some embodiments, the spring actuator may reduce the pressure or prevent pressure increment.

According to some embodiments, the syringes may have seals to prevent aspirated mucus from spilling out of the syringe after use. According to some embodiments, the device kit may contain one or more syringe seals. According to some embodiments, the syringes may contain some of the patient's samples. According to some embodiments, the syringes may contain a sticker on which the user can write. According to some embodiments, the syringes may contain instructions or warnings, such as do not use with drugs, drug warnings or drug instructions.

According to some embodiments, the device may contain more than one syringe. According to some embodiments, the syringes may be connected to the device by T or Y connector. According to some embodiments, the syringes can be connected to a connector with more than three ports. According to some embodiments, some of the ports might have a one-way valve such as a duckbill valve. Such a valve may prevent backflow of gas or liquids from one syringe to the other. According to some embodiments, the syringes may contain a handle or a gunlock that will prevent backflow from one syringe to the other. According to some embodiments, the syringes may contain a syringe stop cock. According to some embodiments, the syringes may be safety syringes with maximal pressure limitation. According to some embodiments, one syringe might be used for irrigation and another one for aspiration. According to some embodiments, the aspiration syringe is bigger than the irrigation syringe. According to some embodiments, the device might contain more than one syringe for more than one irrigation, at least one of those syringes containing a drug or therapeutic substance. According to some embodiments, the device might be used for a sequence of irrigations with different drugs or therapeutic substances in separate syringes.

According to some embodiments, the syringes or at least part of the irrigation may contain a therapeutic substance, a drug, phage or bacteria for sinus wash. According to some embodiments, the drug or substance may be steroids, decongestants, analgesics, anesthetic, antibiotics, antibacterial substance, antiviral substance, antifungal substance, anti-inflammatory substance, mucolytic substance, surfactant, saline, hyperosmolar saline, acidic substance, basic substance, abrasive material, each possibility represents a separate embodiment.

According to some embodiments, there is provided a method to treat sinusitis: Step of removing mucus from the sinus by lavage using a rotating/grinding wire to stir the lavage liquids. Step of filling the sinus with a drug. Step of washing antiseptics or drug or medication from the sinus. Alternatively, this last step can be disabling of the drug.

According to some embodiments, there is provided a method to treat sinusitis: Step of removing mucus and bacteria from healthy sinus by lavage using a rotating/grinding wire to stir the lavage liquids. Step of removing mucus from not healthy sinus by lavage using a rotating/grinding wire to stir the lavage liquids. Step of filling the unhealthy sinus with mucus and bacteria from the healthy bacteria. According to some embodiments, the healthy sinus can be of the same patient, or it can be a sinus of a different patient. According to some embodiments, the last step can comprise insertion of a sustained release drug into the sinus.

According to some embodiments, provided is a method to treat sinusitis: Step of removing mucus and bacteria from healthy sinus by lavage using a rotating/grinding wire to stir the lavage liquids. Step of removing mucus from unhealthy sinus by lavage using a rotating/grinding wire to stir the lavage liquids. Step of filling the unhealthy sinus with a therapeutic agent, antiseptic, medication or other drug. Step of washing the therapeutic agent, antiseptic, medication or other drug or from the unhealthy sinus. Alternatively, this last step can be disabling of the drug. Step of filling the unhealthy sinus with mucus and bacteria from the healthy bacteria. According to some embodiments, the healthy sinus can be of the same patient, or it can be a sinus of a different patient. According to some embodiments, the last step can comprise insertion of a sustained/controlled release drug into the sinus.

According to some embodiments, the methods can comprise the step of sending the mucus to a lab. According to some embodiments, the methods can comprise a step of healthy sinus bacteria diagnosis. According to some embodiments, the methods can comprise a step of unhealthy sinus bacteria diagnosis. According to some embodiments, bacteria diagnosis can influence a treatment decision, such as using or not using the aspirated mucus or using an additional drug. According to some embodiments, the methods can comprise additional steps of using an additional therapeutic agent, antiseptic, medication or other drug, and additional steps of lavage.

According to some embodiments, the therapeutic substance, drug, phage or bacteria may be instilled within a carrier's medium or a vehicle. According to some embodiments, the carrier's medium or vehicle provides sustained or controlled release to the therapeutic substance, drug, phage or bacteria. According to some embodiments, the medium or vehicle may be a gel, a foam, an aerosol, an emulsion, a suspension, an adhesive, or other capsulation mechanisms, all in separate embodiments. According to some embodiments, the medium or vehicle of the therapeutic substance, drug, phage or bacteria may be injected into the sinus. According to some embodiments, the medium or vehicle of the therapeutic substance, drug, phage or bacteria may be injected into the sinus during or after sinus lavage. According to some embodiments, the medium or vehicle may release the therapeutic substance, drug, phage or bacteria within the sinus for a period of more than one day, one week, one month, one quarter, one year all in separate embodiments. According to some embodiments, the medium or vehicle may resist the sinus mucosal clearance, and sustain in the sinus for a period of more than one day, one week, one month, one quarter, one year all in separate embodiments. According to some embodiments, the medium may change its properties after being inserted into the sinus. According to some embodiments, the medium may increase its resistance to flow, its viscosity, its adhesiveness its rigidity, or solidify, after being inserted into the sinus. For example, according to one embodiment, the drug medium is liquid during insertion within the syringe and cannula, but it solidifies to foam within the sinus, by the body temperature. According to some embodiments, the medium can control the release of the therapeutic substance into the sinus cavity by exterior stimuli, such as RF radiation.

According to some embodiments, the carrier's medium or a vehicle may be suitable to provide bacteria a supportive environment. According to some embodiments, the carrier's medium or a vehicle may be suitable to provide agar and nutrition to bacteria. According to some embodiments, the carrier's medium or a vehicle may be suitable to provide a supportive environment to creation bacteria, that is not supportive to other kinds of bacteria. According to some embodiments, the carrier's medium or a vehicle can comprise selective growth factors, such as oxygen enrichment, proteins, pH level or sugars. According to some embodiments, the carrier's medium or a vehicle may be or have the properties of healthy nasal/sinus mucus. According to some embodiments, the carrier's medium or a vehicle may be healthy nasal/sinus mucus diluted with saline or water.

According to some embodiments, the above-mentioned bacteria, bacterial supplement, bacterial interference, bacterial treatment or probiotic might include: *viridans Streptococci*, α-*Streptococcus*: Alpha-hemolytic, *Pneumococci*, The *S. viridans* group: alpha-hemolytic, Beta-hemolytic, *Enterococci Streptococci, Streptococci, Streptococci*, Aerobic alpha-hemolytic *Streptococci* (such as *Streptococcus mitis* and *Streptococcus sanguis*) or nonhemolytic such as Ab1III. *Streptococcus oralis* Parker and *S. oralis, Prevotella melaninogenica, Peptostreptococcus* sp, anaerobius, Non-hemolytic *Streptococci, Corynebacterium* spp. Such as (Co304), *Corynebacterium* such as *Corynebacterium* sp (API Coryne bioprofile; 5100304), *Prevotella* sp, *Staphylococcus aureus* such as 502A of *S. Aureus*, Coagulase-negative *Staphylococcus, Staphylococcus epidermidis, Streptococcus salivarius, Streptococcus mutans, Enterococcus faecalis, Streptococcus pneumoniae, Streptococcus pyogenes, Neisseria* sp., *Neisseria meningitidis, Enterobacteriaceae* (*Escherichia coli*), *proteus* sp., *Pseudomonas aeruginosa, Haemophilus influenzae, Haemophilus* spp., *Lactobacillus* sp., *Clostridium* sp, *Corynebacteria, Mycobacteria, Actinomycetes, Spirochetes, Mycoplasmas, S. agalactiae, S. anginosus, S. bovis, S. canis, S. constellatus, S. dysgalactiae, S. equinus, S. iniae, S. intermedius, S. milleri, S. mitis, S. mutans, S. oralis, S. parasanguinis, S. peroris, S. pneumoniae, S. pseudopneumoniae, S. pyogenes, S. ratti, S. salivarius, S. tigurinus, S. thermophilus, S. sanguinis, S. sobrinus, S. suis, S. uberis, S. vestibularis, S. viridians, S. zooepidemicus, Corynebacteria, Cardiobacterium* spp, *Eikenella corrodens, Kingella* spp, *Kingella kingae, Moraxella* spp, *Moraxella catarrhalis, Mycoplasma pneumoniae, Neisseria* spp, *Neisseria cinerea, Neisseria lactamica, Neisseria meningitides, Neisseria mucosa, Neisseria sicca, Peptococcus* spp, *Selenomonas sputigena, Streptobacillus* spp, *Streptococcus mitis, Streptococcus pyogenes*, together or separately as different embodiments.

According to some embodiments, the dug may include Acesulfame K, Acetamide MEA (monoethanolamine), Acetic acid, Activated charcoal, African palm oils, Alcohol, Alcohol (ethyl alcohol), Allantoin, Almond meal, Aloe vera, Aluminum hydroxide, Aluminum magnesium hydroxide stearate, Aluminum oxide, Aluminum pigment, Aluminum sulfate, Ammonium phosphate, *Angelica* sp., Aqueous wheat extract, Arachidyl alcohol, Ascorbyl palmitate (Vitamin C ester), Ascorbyl tetraisopalmitate (Vitamin C ester), Avocado oil, Bacitracin, Beeswax, Behenyl alcohol (docosanol, Abreva), Benzalkonium cetyl phosphate, Benzalkonium chloride, Benzocaine, Benzoic acid, Benzyl alcohol, Betaines (various forms), Bisabolol (chamomile oil), Bismuth subgallate, Bismuth tribromophenate, Borneol, Butylated Hydroxytoluene (BHT), Butylene glycol, *Butyrospermum parkii*, Cadexomer iodine, Calamine, Calcium, Calcium carbonate, Calcium chloride, Calcium oxide, Calcium sulfate, Camelia sinensis, Candelilla wax, Capryloyl glycine, Carvacrol, Centella asiatica, Ceramide, Ceteareth-10 phosphate, Cetearyl alcohol (Cetostearyl alcohol), Ceteth-20, Cetyl alcohol, Cetyl dimethicone copolyol, Cetyl palmitate, Cetylpyridinium chloride, Chlorhexidine, Chlorhexidine gluconate, Chlorine dioxide, Chlorophyllin copper complex sodium, Cholesterol, Chromium chloride, Citric acid, Citris grandis extract, Cloflucarban, Cobalt chloride, Cocoamphodiacetate, Colloidal silica, Combination of potassium vegetable oil, solution, phosphate sequestering agent, and triethanolamine, Conjugated linoleic acid, Copper, Copper chloride (cupric chloride), Crystal violet, Cupuacu butter, Cyclodextrin, Cyclomethicone, DEA Cetyl phosphate, Decanoic acid (capric acid), Dehydroacetic acid, Dialkyl carbamoyl chloride, Diazolidinyl urea, Dicetyl phosphate, Diisopropyl adipate, Dimethicone, Dipolyhydroxystearate, Dissolved oxygen, DMDM hydantoin, EDTA, Ethanol, Ethoxydiglycol, Ethylene glycol monostearate, Ethylhexyl glycerin, Ethylhexyl palmitate, Eucalyptus oil, Eugenol, Extracts of licorice (deglycyrrhizinated), Ferric chloride Hexahydrate, Ferric oxide, Fluorosalan, Fruit extract, Fumed silica, Gentian violet, Germaben II, Glycerin (glycerol), Glyceryl monolaurate, Glyceryl monostearate, Glyceryl stearate, Glycyrrhetinic acid (licorice extract), Guar gum (Cyaiuopsis letragonolobus), Gum mastic, Hectorite clay, Hexachlorophene, Hexyl laurate, Hydrochloric acid, Hydrocortisone, Hydrogen peroxide, Hydrogenated castor oil, Hydrogenated lecithin, Hydroquinone, Hydrous lanolin, Hydroxypropyl bispalmitamide MEA, (ceramide), Hydroxypropyl guar, Hypochlorous acid, Iodine, Iodine complex (ammonium ether sulfate, and polyoxyethylene sorbitan, monolaurate), Iodine complex (phosphate ester of, alkylaryloxy polyethylene glycol, Iodoform, Iodophors (Iodine-containing ingredients), Iron (various forms), Iron sulfate, Isohexadecane, Isopropyl alcohol, Isopropyl alcohol, Isopropyl myristate, Isopropyl sorbate, Kaolin, Karaya gum, Keratin, Konj ac flour, Lactic acid, Lavender, Lecithin, Lemon, L-glutamic acid, Lidocaine, Light mineral oil, Liquid Germall Plus (propylene glycol, diazolidinyl urea, iodopropynyl, butylcarbamate), Lyophilized formulate porcine plasma, Magnesium aluminum silicate, Magnesium oxide, Magnesium stearate, Magnesium sulfate, Malic acid, Maltodextrin, Manganese chloride, Manganese oxide, Mannitol, Meadowsweet extract. Menthol, Methyl salicylate, Methyl triethoxysilane (MTES), Methylal, Methylbenzethonium chloride, Methylene blue, Mineral oil, Molybdenum chloride, Myristyl myristate, Myrtillus extract, Nonylphenoxypoly (ethyleneoxy), Ethanoliodine, Oak extract, Oat glucan, O-cymen-5-ol (Biosol), Olive oil, Ozone, Palm glycerides, Palmitamide MEA, Palmitic acid, Panthenol FCC (form of vitamin B), Parabens (various forms), Paraffin, Pentalyn-H (Pentaerythritol ester of rosin), Pentylene glycol, Petrolatum, Phenol (greater than 1.5 percent), Phenol (less than 1.5 percent), Phenoxyethanol, Phosphoric acid, Phosphorus pentoxide, Piroctone olamine, Poloxamer—iodine complex, Polyaminopropyl biguanide (PAPB), Polygonum cuspidatum, Polyhexamethylene biguanide, Polyhexamethylene biguanide (PHMB, polyhexanide), Polymyxin B sulfate, Polyricinoleate, Polyvinyl pyrrolidone-iodine, Potassium ferrate, Potassium iodide, Potassium iron oxyacid salt, Potassium sorbate, Povidone iodine, Povidone USP (Plasdone K 29-32), Povidone-iodine 5 to 10 percent, Propyl gallate, Propylene glycol, Pyroglutamic acid, Quaternium 15, RADA-16 peptide, Rubidium chloride, Saccharin, Salicylic Acid, Salicylic acid, Sandalwood oil, Sarcosine, Secondary amyltricresols, Shea butter, Silver (various forms), Silver sulfadiazine, Sodium benzoate, Sodium citrate, Sodium fluoride, Sodium hypochlorite, Sodium lactate, Sodium metabisulfite, Sodium oxychlorosene, Sodium selenite, Sodium sulfate, Sodium tetraborate (Borax), *Solanum lycopersicum* (tomato) extract, Sorbic acid, Sorbitan sesquioleate (Arlacel C), Sorbitol, Soy protein, Squalane, Steareth-10, Stearic acid, Styrax, Sucralfate (sucrose octasulfate, aluminum, hydrochloride), Sucrose, Sucrose laurate, Sulfur, dioxide, Tara Gum, Tartaric acid, Tea tree oil, Tea tree oil, Telmesteine, Theobroma Grandiflorum seed butter, Thrombin, Thymol, Titanium dioxide, Titanium oxide, Tonalin FFA 80, Transcinnamaldehyde, Tribromsalan, Triclocarban, Triclosan, Triethanolamine (TEA), Triglycerol (polyglycerol-3), Triiodide resin, Triple dye, Trolamine, Tromethamine USP, Undecoylium chloride iodine complex, *Vaccinium* (blueberry), Vegetable oil, Vitamin C (ascorbic acid), Vitamin E (tocopherol), *Vitis vinifera* (grape), White petroleum, Wintergreen fragrance, Wood pulp core, Xanthan gum, Xylitol, Zinc (various forms), Zirconium oxide, Azithromycin, Levofloxacin, Ciprofloxacin Neo/Poly/Dex Tobramycin Dexamethasone, Azelastin, Prednisolone, Olopatadine, Garlic, Carvacrol, Olive/Olive leaves extracts, Turmeric, Echinacea, Ginger, Goldenseal, Oregano Oil, Cayenne Pepper, Colloidal Silver, Grapefruit Seed Extract, Manuka Honey, Pau d'Arco, Neem, Turmeric, Pau D'arco, Apple Cider Vinegar, Grapefruit Seed Extract, Virgin Coconut Oil, Mepolizumab (IL-5 antagonist), Montelukast, Doxycycline, together or separately as different embodiments.

According to some embodiments, the user may use only one component of the above stated substances during or after sinus lavage. According to some embodiments, the user may use more than one component of the above during or after sinus lavage. According to some embodiments, the user may use more than one component of the above during or after sinus lavage in more than one sinus lavage. For example, the user may lavage the sinus with saline and steroids, and only then lavage it again with bacteria and steroid gels.

According to some embodiments, the abrasive material contains small hard particles. According to some embodiments, the abrasive material may increase mucosa, polyps, bacteria and biofilm removal from the sinus wall. According to some embodiments, the abrasive material may be inserted into the sinus within gas or liquid. According to some embodiments, the abrasive material may dissolve, degrade and or be evacuated from the sinus after lavage. Most abrasive materials such as silica might cause harm to the sinus and nasal mucosa, unless it is removed. According to some embodiments, the abrasive material may be a salt. According to some embodiments, the abrasive material may be magnesium such as magnesium oxide.

According to some embodiments, all the above can be inserted into the sinus via another mechanism instead of a syringe, such a capsule or irrigation machine, during or after sinus lavage.

According to some embodiments, the syringes or other aspirated material cavity or capsule, may contain a medium for bacterial growth, such as a medium for aerobic or anaerobic bacteria.

According to some embodiments, the syringes, other aspirated material cavity or capsule, may contain a pH measurement apparatus, such as pH litmus paper. According to some embodiments, the device kit may contain pH measurement equipment such as pH litmus paper. According to some embodiments, the user may use the pH level to distinguish between aerobic or anaerobic bacteria. The user may change the medium for bacterial growth and the treatment accordingly. For example, he may use different antibiotics and bacteria supplements.

According to some embodiments, the syringes, other aspirated material cavity or capsule, may contain a c-reactive protein measurement and or Erythrocyte sedimentation rate apparatus such as CRP or ERS strips. According to some embodiments, the device kit may contain a c-reactive protein or Erythrocyte sedimentation rate measurement apparatus such as CRP or ERS strips. and method embodiments the user may change the treatment according to those measurements. For example, he may use different antibiotics, and bacteria supplements.

According to some embodiments, and method embodiments the syringes or kit might include also the use of measurement for one or more of the following: White Blood Cells—WBC/Leucocytes indication for contamination, Neutrophils—NEUT indication for contamination, Lymphocytes—LYMPH/LYM indication for viral contamination, Monocytes—MONO indication for viral contamination, Basophils—BASO, Eosinophils—EOSIN/EOS indication for allergy, a2-macroglobulin (as a marker for plasma contamination) lactoferrin (as a marker for glandular secretion), lactate dehydrogenase (as a marker for tissue injury), interleukin (IL)-1b, IL-8, tumour necrosis factor-a, eosinophil cationic protein and tryptase (as indicators for tissue inflammation) together or separately as different embodiments.

According to some embodiments, the device and method might include at least one of the following bacteria diagnostic measures in the syringe or in other cavity: PHmeasurement, Electrical conductivity, Resonance frequency, Mass spectrometry, Spectroscopy, Bacterial DNA sequencing, and culture growing, Antibiogram, together or separately as different embodiments.

According to some embodiments, the measurements might include Nitrogen Dioxide NO2 Gas measurement such as with Dioxide NO2 Gas Analyzer. According to some embodiments, the measurements might include Nitric oxide NO Gas measurement such as with Chemiluminescence or NIOX Mino. According to some embodiments, the measurements might include artificial nose measurement or other apparatus that identify bacteria, cell, pathogens or its product in molecules in aspirated gas from the sample.

According to some method embodiments, the user might use the above mentioned measurements to make a decision whether the aspirated sample contains bacteria, fungi viruses, or no pathogen. According to some method embodiments, the user might use the above mentioned measurements to make a decision whether the aspirated sample contains aerobic or anaerobic bacteria. According to some method embodiments, the user might use the above mentioned measurements to make a decision on the most appropriate treatment. According to some method embodiments, the user might use the above mentioned measurements to make a decision on the most appropriate antibiotic treatment. According to some method embodiments, the user might use the above mentioned measurements to make a decision on the most appropriate bacterial supplement. According to some method embodiments, the user might use the above mentioned measurements to make a decision on the most appropriate allergy treatment.

According to some embodiments, all the above can be extracted out of the sinus via another mechanism instead of a syringe, such as an aspiration machine and be processed in a capsule or other container.

According to some embodiments, provided is a method to treat sinusitis: Step of removing mucus from the sinus by lavage using a rotating/grinding wire to stir the lavage liquids. Step of filling the sinus with antiseptics or drug or medication to reduce microorganism concentration in the sinus. Step of washing antiseptics or drug or medication from the sinus. Alternatively, this last step can be disabling the antiseptics or drug or medication.

Antiseptics and Bactericidal may include: Alcohols, or "surgical alcohol" such as ethanol (60-90%), 1-propanol (60-70%) and 2-propanol/isopropanol (70-80%) or mixtures of these alcohols. Surfactants. Anionic, or zwitterionic surfactants. PEG-80 Sorbitan laurate, Cocamidopropyl betaine, and Sodium Trideceth Sulphate (Johnson & Johnson Baby Shampoo). Citric acid such as Zwitterionic Surfactant Cationic surfactants such as quaternary ammonium cations such as benzalkonium chloride 0.05-0.5%, chlorhexidine 0.2-4.0% or octenidine dihydrochloride 0.1-2.0%, Chlorhexidine gluconate. Quaternary ammonium compounds, (quats or QACs), such as, cetyl trimethylammonium bromide, cetylpyridinium chloride, and benzethonium chloride. cetyl trimethylammonium chloride, didecyldimethylammonium chloride and others, non-quaternary compounds, such as chlorhexidine, glucoprotamine, octenidine dihydrochloride etc. Chlorhexidine and Octenidine. Boric acid. Brilliant green (triarylmethane dye). Hydrogen peroxide such as 6% or lower. peracetic acid (Hydrogen peroxide and acetic acid). Iodine such as: Tincture of iodine/Lugol's iodine (Iodine & alcohol. 1% iodine or less. iodinated nonionic surfactants), Povidone-iodine (an iodophor, complex of povidone, a water-soluble polymer, with triiodide anions I3—, containing about 10% of active iodine). Manuka honey. Mercurochrome Organomercury antiseptics such as bis-(phenylmercuric) monohydrogenborate (Famosept). Octenidine dihydrochloride. (0.1-2.0%). Octenidine. Chlorhexidine. 1&2-phenoxyethanol. Phenolic substances such as Phenol, cresols, TCP, Lysole. halogenated (chlorinated, brominated) phenols, such as hexachlorophene, triclosan, trichlorophenol, tribromophenol, pentachlorophenol, Dibromol and salts thereof. thymol, hexachlorophene, triclosan, and sodium 3,5-dibromo-4-hydroxybenzenesulfonate (Dibromol). Polyhexanide (polyhexamethylene biguanide, PHMB). Sodium chloride (salt) Sodium hypochlorite boric acid. Calcium hypochlorite. Sodium bicarbonate (NaHCO3). Balsam of Peru. Xylitol. Chlorine such as hypochlorites, chloramines, dichloroisocyanurate and trichloroisocyanurate, wet chlorine, chlorine dioxide. Active oxygen and peroxides, such as peracetic acid, potassium persulfate, sodium perborate, sodium percarbonate, and urea perhydrate. oxidizers, such as ozone and permanganate solutions. acids such as phosphoric, nitric, sulfuric, amidosulfuric, toluenesulfonic acids. Alkalis such as sodium, potassium, calcium hydroxides. Tea tree oil.

According to some embodiments, Antimicrobial may be Nanomaterials Antimicrobial or Nanoparticles, (i.e., metal, metal oxide, and organic nanoparticles). According to some embodiments, antibacterial Nanomaterials interact electrostatically with the bacterial membrane causing membrane disruption.

Inorganic Nanoparticles includes Metal oxide nanoparticles such as silver (Ag), iron oxide (Fe3O4), Superparamagnetic Iron Oxide, titanium oxide (TiO2), copper oxide (CuO), zinc oxide (ZnO), Magnesium oxide (MgO) as MgX2, MgF2, Nitric oxide (NO) nanoparticles, Polyethylenimine and quaternary ammonium compounds, Chitosan & polyguanidines, Aluminum Oxide.

Organic Nanoparticles includes: Poly-ε-lysine, Quaternary Ammonium Compounds, Cationic Quaternary Polyelectrolytes, N-Halamine Compounds, Polysiloxanes, Benzoic Acid, Phenol, and p-Hydroxy Benzoate Esters, Quaternary Phosphonium or Sulfonium, Triclosan, 5-Chloro-8-hydroxy-quinoline, Peptides, Organometallic Polymers, Polymeric Nanosized Antimicrobials, Polycationic Nanoparticles, Chitosan.

According to some embodiments, the device comprises a needle capable of puncturing the sinus wall. According to some embodiments, the needle is straight and, according to some embodiments, it is a curved needle. According to some embodiments, the device's needle is mounted on part of the device distal tip. According to some embodiments, the device's needle is mounted on the tubular guide or bent tube. According to some embodiments, the device's needle is the tubular guide or bent tube (the needle is replacing the tubular guide or bent tube). According to some embodiments, the device needle is the extension of the tubular guide or bent tube. According to some embodiments, the device's needle is straight and, according to others, it is bent. According to some embodiments, the device needle is capable of containing at least some of the cannula. According to some embodiments, the device's needle is mounted on the tubular guide or bent tube from within it. According to some embodiments, the device's needle is mounted on the cannula. According to some embodiments, the device's needle is the cannula (the needle is replacing the cannula). According to some embodiments, the device's needle is the extension of the cannula. According to some embodiments, the device's needle is capable of containing at least some of the grinding wire. According to some embodiments, the bent tube is inserted into the sinus after needle puncture. According to some embodiments, the bent tube is inserted into the sinus after needle puncture. According to some embodiments, the cannula is inserted into the sinus after needle puncture. According to some embodiments, the cannula distal tip bends or changes its orientation within the sinus after being inserted. According to some embodiments, the grinding wire is inserted into the sinus after needle puncture. According to some embodiments, the wire distal tip bends or changes its orientation within the sinus after being inserted.

According to some embodiments, the needle is inserted into the sinus, the wire is inserted into the needle, the irrigation liquids are inserted and or aspirated via the needle, and the guiding tube that surround the cannula aspirates the spilled liquids of the punctured opening.

According to some embodiments, the device needle has the diameter of 3 mm, as a conventional cannula. According to some embodiments, the device needle has the diameter of equal or less than 3 mm According to some embodiments, the device needle has the diameter of equal or less than 2 mm According to some embodiments, the device needle has the diameter equal or less than 1 mm. As in the small diameter cannula description above, the grinding wire enables reduction of the mucus viscosity and thus facilitate suction via smaller diameter than typically applied today. Using smaller diameter puncturing might enable faster mucosal recovery and might cause less complications such as pain, bleeding, contamination, or neural puncturing. Safer puncturing may be important in cases, which the user finds it difficult to find the natural sinus opening or penetrate it. According to some embodiments, the sinus puncturing is not limited to the maxillary and sphenoid sinuses but it also can be used to puncture every nasal cavity or head sinus, such as the ethmoid sinus cells, the ethmoid bola, the mastoid sinus, the middle ear, etc.

According to some embodiments, the device needle can be advanced forward and into the sinus wall by unlashing a tensed spring. According to some embodiments, the distance of the needle movement forward and into the sinus wall is limited by a stopper or a restraining mechanism. According to some embodiments, the distance is less than 20 mm, 10 mm, 5 mm, 3 mm, 2 mm, all in separate embodiments. The mechanism may assist the user to avoid over penetration into the sinus. Orbital puncturing during maxillary sinus puncturing is a rare but very disturbing complication, well documented in the literature.

According to some embodiments, the device's needle can be advanced forward and into the sinus wall by the cannula handle. According to some embodiments, the device's needle can be advanced forward and into the sinus wall by a motor. According to some embodiments, the device's needle can be advanced forward and into the sinus in screwing motion. According to some embodiments, the device's needle has threading. According to some embodiments, the device's needle has a drill in a tube shape, that is surrounding the cannula or the grinding wire. According to those embodiments, the cannula or the grinding wire is inserted into the sinus cavity after the drill is drilled into the sinus. According to some embodiments, the device's drill or the device's needle is pushed into the sinus wall with a pneumatic hammer mechanism.

According to some embodiments, the cannula can be detached from the device and stay within the sinus for further lavages or as drains. According to some embodiments, the threaded needles can be detached from the device and stay within the sinus for further lavages or as drains. According to some embodiments, the cannula or threaded needles can be reattached to the device. According to those embodiments, a new wire can be inserted into the cannula for additional mucus stirring and grinding during irrigation and aspiration.

According to some embodiments, the cannula and/or guiding tube and or grinding wire may be inserted into a sinus via the sinus wall or via the sinus floor. According to some embodiments, the cannula and/or guiding tube and or grinding wire can be inserted into a maxillary sinus cavity via a molar tooth or via a tooth hole, or via patient gum (as the ancient Egyptians drained the maxillary sinuses). According to some embodiments, the grinding wire can rotate within the sinus to grind mucus and or mucosa and or polyps.

According to some embodiments, the device may comprise an additional handle (endoscope grasping handle) that enables the user to grasp the handle and an endoscope with the same hand. According to some embodiments, the handle may be attached to the device casing with a snap mechanism.

Throughout the following description, similar elements of different embodiments of the device are referenced by element numbers differing by integer multiples of 1000. For example, a device of FIG. 1 is referenced by the number 1000, and a device of FIG. 2, which corresponds to device 1000 of FIG. 1, is referenced by the number 2000. For another example, a guiding tube of FIG. 1 is referenced by the number 1602, and a guiding tube of FIG. 2, which corresponds to guiding tube 1602 of FIG. 1, is referenced by the number 2602.

Figure 1B:
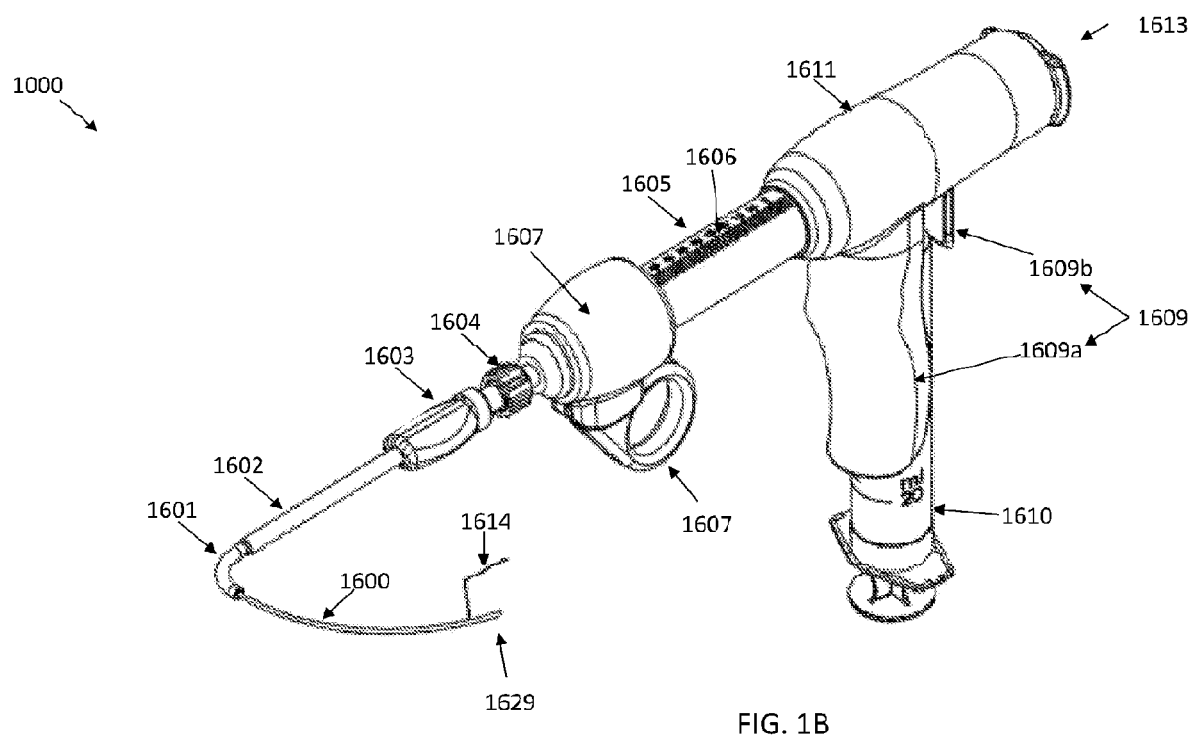

Reference is now made to FIGS. 1A and 1B which schematically illustrate a device 1000 that may be used for treating a paranasal sinus condition in a retracted and opened configurations, respectively, according to some embodiments.

Device 1000 includes a guiding tube 1602 configured for insertion into a subject's nose such that a distal end thereof faces the subject's ostium; a flexible hollow cannula ("cannula") 1600 at least partially housed within guiding tube 1602 and movable therein such as to protrude distally therefrom and intrude through the ostium into a sinus cavity of the subject; and a flexible wire 1614 at least partially housed within cannula 1600 and configured to move therein such as to protrude distally therefrom into the sinus cavity and to grind, chop and/or stir material present in the sinus cavity and/or inside cannula 1600.

Device 1000 may further include a distal casing section 1605, and a proximal casing section (which may also be referred to as housing) 1611.

Guiding tube 1602 includes a distal end 1601 shaped for insertion into a nostril of a patient. Optionally, distal end 1601 is at least partially bendable such as to face a natural opening of a paranasal sinus following insertion to the nostril. Alternatively or additionally, distal end 1601 may be bent/curved. According to some embodiments, distal end 1601 is bendable by the user (for example by the user's hands). According to some embodiments, distal end 1601 is bendable using a bending jig (not shown).

Optionally, the bend/curve is shaped such as to allow/facilitate insertion of distal end 1601 into a sinus of a patient. Optionally, the insertion is into a maxillary sinus, a frontal sinus, a sphenoid sinus, or Eustachian tubes. Each possibility represents a separate embodiment, and may be combined at will. In a non-limiting example, distal end 1601 may be bent according to a desired application such as to an angle ranging from 70 to 110 degrees for insertion into the maxillary sinus, an angle ranging from 0 to 30 degrees for insertion into the sphenoid sinus, an angle ranging from 60 to 80 degrees for insertion to the frontal sinus, an angle ranging from 30 to 70 degrees for insertion into the eustachian tubes.

Optionally, guiding tube 1602 having a distal end 1601 with a predefined bend of a desired angle may be releasably applied to device 1000 according to a desired insertion target (e.g., a maxillary sinus, a frontal sinus, a sphenoid sinus or eustachian tubes). Optionally, guiding tube 1602 is releasably connected to distal casing section 1605 of device 1000, with one or more connectors selected from connector 1603 and connector 1604. Optionally, one or more connectors 1603 and 1604 fix guiding tube 1602 in a selected orientation. Suitable connector types include but are not limited to luer lock connector. According to some embodiments, the connection of guiding tube 1602 to distal casing section 1605 is sealed to air and liquid flow.

Optionally, guiding tube distal end 1601 includes an atraumatic tip (not shown) such as having a smooth surface, a round or a ball shape. Optionally distal end 1601 includes one or more openings for irrigation and or aspiration. According to some embodiments, a lens, a light source, a camera or any combination thereof may be contained within or mounted on distal end 1601.

Optionally, cannula 1600 is operably connected to a cannula handle 1607. Optionally, cannula handle 1607 is operated to move cannula 1600 within guiding tube 1602 proximally and distally, and optionally (as demonstrated in FIG. 1B) to protrude distally from tubular member distal end 1601. Optionally, visual distance indications 1606 are marked on distal casing section 1605. Those marks give the user visual feedback about cannula 1600 position. According to some embodiments, these marks may indicate to the user whether the cannula was inserted into a sinus opening (and optionally, how far along) or not. Optionally, cannula handle 1607 includes and is controlled by a trigger 1608 which moves cannula 1600 back and forward when pressed on, and prevents movement when it is not pressed. Suitable mechanism for controlling cannula movement may include, but is not limited to, a ratchet lock. According to some embodiments, cannula handle 1607 and/or trigger 1608 provide the user tactile feedback from cannula's 1600 distal tip 1629, via the cannula actuation mechanism. According to some embodiments, such tactile feedback may indicate the user whether the cannula was inserted into a sinus opening, or whether the cannula is being pushed into undesired location, or whether the cannula is pushed in undesired force (such as pushed to strongly, which might cause injury).

Device 1000 may further include a gripper 1609, coupled to proximal casing section 1611. Gripper 1609 is intended to be held by one hand of a user (such as a doctor, nurse or a technician), optionally in a pencil like grip, or a gun like grip and is designed accordingly. Optionally, the gripper has a length ranging from 5 centimeters (cm) to 50 cm, 5 cm to 40 cm, 5 cm to 30 cm, 5 cm to 25 cm, 5 cm to 20 cm, 5 cm to 18 cm, 5 cm to 15 cm, 8 cm to 50 cm, 8 cm to 40 cm, 8 cm to 30 cm, 8 cm to 25 cm, 8 cm to 20 cm, 8 cm to 18 cm, 8 cm to 15 cm, 10 cm to 25 cm, 10 cm to 25 cm, 10 cm to 20 cm, 10 cm to 18 cm, or 10 cm to 15 cm. Each possibility represents a separate embodiment of the present invention. Gripper 1609 may include a distal gripper 1609a and proximal gripper 1609b enabling the user to hold gripping handle 1609, such that two, three or four fingers of a hand may conveniently interface with a distal surface of distal gripper 1609a and a thumb of a hand may conveniently interface with a proximal surface of proximal gripper 1609b. Optionally, the index finger of the hand may be fitted to and operate trigger 1608 of cannula handle 1607. According to some embodiments, gripping handle 1609 is designed to hold a syringe 1610 between distal gripper 1609a and proximal gripper 1609b, or other irrigation/aspiration line other than syringe 1610, such as a tube, a pump or a combination thereof. Optionally, this design is further utilized to prevent the user from using unintended syringe such as too big syringe by miss fitting unintended syringe geometric properties. According to some embodiments, gripper 1609 may enable the user to hold gripping handle 1609, such that one, two or three fingers of a hand may conveniently hold syringe 1610.

Device 1000 may further include a wire handle 1612. Wire handle 1612 is operably connected to wire 1614 and configured to move wire 1614 within cannula 1600 and optionally, protrude therefrom. According to some embodiments, wire handle 1612 or housing 1611 includes visual marks 1612a marked on an outer surface thereof to allow the user visual feedback about wire 1614 position in space. Wire handle 1612 may be coupled to a motor 1613 operably connected to wire 1614 (e.g., via a shaft such as shaft 3615, shown in FIG. 3A) and configured to rotate wire 1614 in high speed. Optionally, motor 1613, is at least partially housed within wire handle 1612. According to some embodiments, after attachment of the motor 1613 to the device, the motor 1613 itself may serves as a wire handle instead of wire handle 1612. According to these embodiments, the motor is functionally connected to the wire 1614 (e.g., via a shaft such as shaft 3615, shown in FIG. 3A) and is configured to move back and forth within casing 1611 as it advances/retrieves wire 1614. According to some embodiments, wire handle 1612 and casing 1611 comprises rails 1675 for orientation and smooth movement of handle 1612 within casing 1611. According to some other embodiments, motor 1613 (which may function as a handle as well as a motor) and casing 1611 comprise rails 1675 for orientation and smooth movement of motor 1613 within casing 1611. Referring to FIG. 1B, each of cannula handle 1607 and wire handle 1612 is in an advanced position such that cannula 1600 protrudes distally from distal end 1601 of guiding tube 1602, and wire 1614 protrudes out (distally) of cannula 1600. Optionally, wire 1614 protrudes out of a side wall of cannula 1600. Optionally, upon protrusion from distal end 1601, cannula 1600 assumes a predefined shape configured to reach a treatment area within a paranasal sinus. Optionally, a distal portion of cannula 1600 is curved or bent.

Optionally, distal tip 1629 of cannula 1600 may be an atraumatic tip (not shown) such as having a smooth surface, a round or a ball shape. Optionally, distal tip 1629 may include one or more openings for irrigation and or aspiration. Optionally, at least a portion of the openings may be side firing apertures (holes). According to some embodiments, distal tip 1629 of cannula 1600 may be closed. According to some embodiments, distal tip 1629 of cannula 1600 may include a taper that direct wire 1614 towards the side-firing apertures. According to some embodiments, a guide wire, a lens, a light source, a camera or any combination thereof may be contained within or mounted on distal tip 1629. According to some embodiments, a camera in distal tip 1629, may be directed towards the rotating wire 1614 area. According to some embodiments, distal tip 1629 of cannula 1600 may have a pre-shaped bend. According to some embodiments, the bend may be about or less than 50, or 40, or 30 or 20 or 10 degrees. Each possibility represents a separate embodiment of the present invention.

Figure 2A:
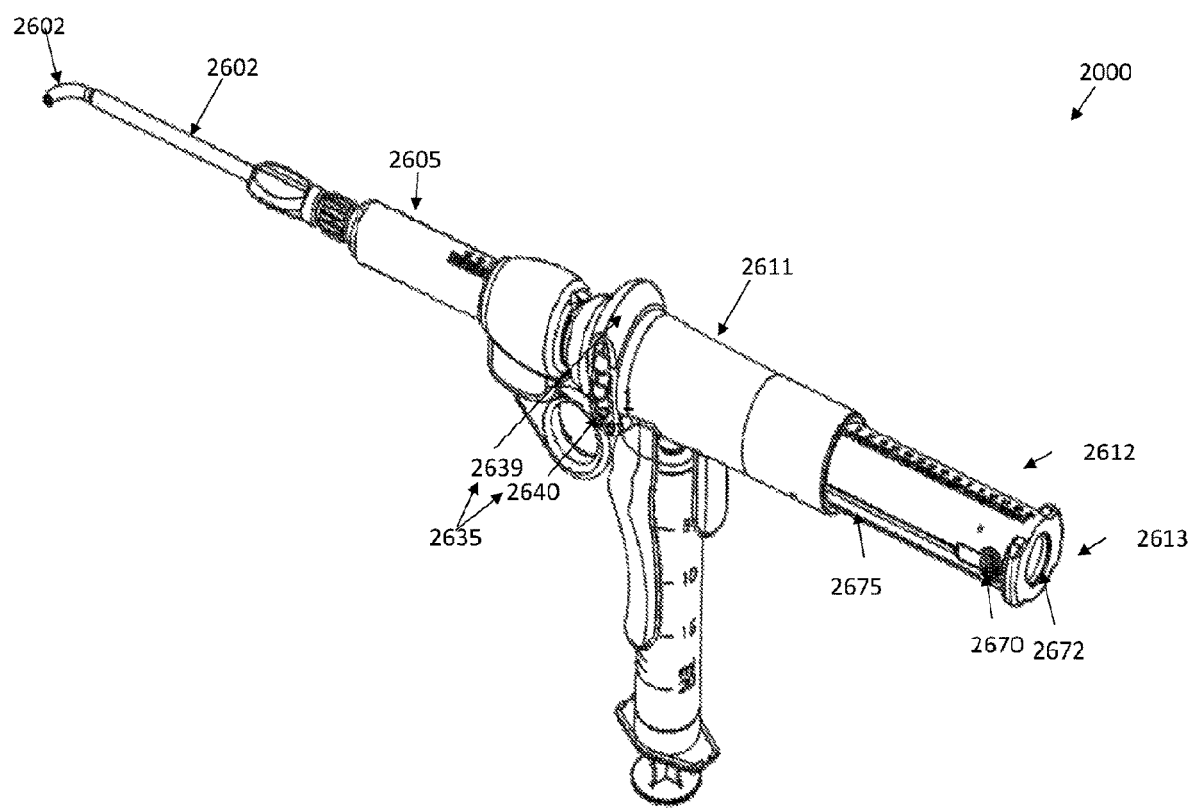
FIGS. 2A and 2B schematically illustrate a device for treating a paranasal sinus condition in retracted and opened configurations, according to some embodiments.
Figure 2B:
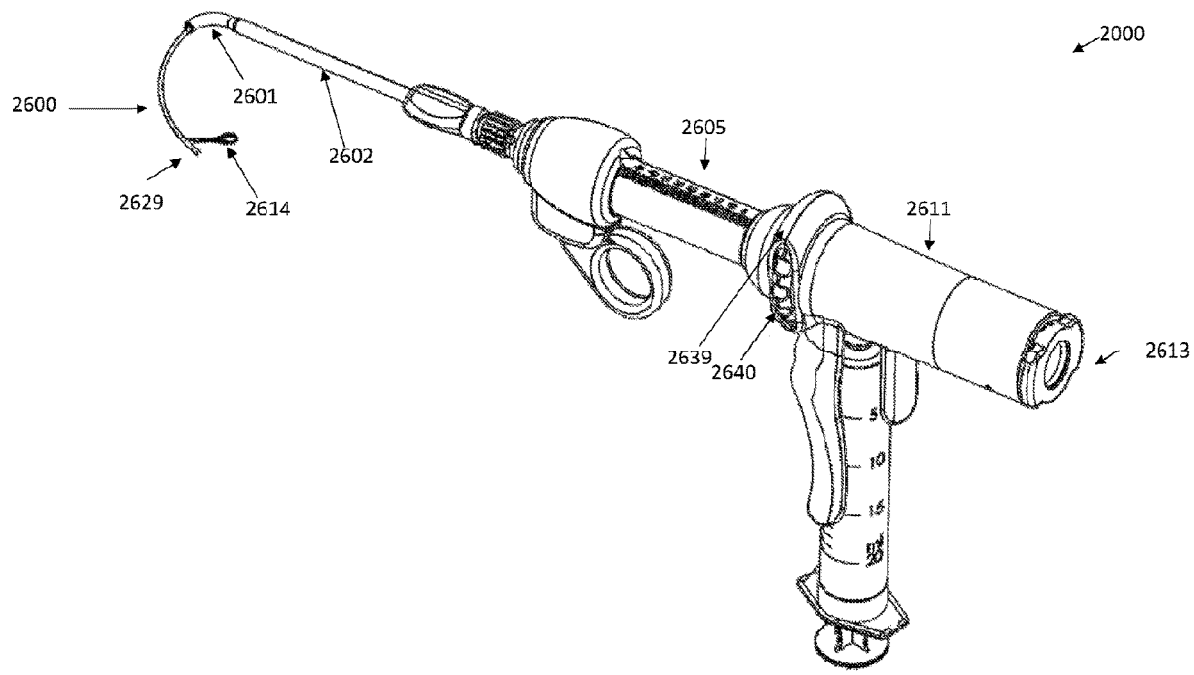

Reference is now made to FIGS. 2A and 2B, which show a device 2000 that may be used for treating a paranasal sinus condition in a retracted and an open configurations, respectively, according to some embodiments. Device 2000 is substantially similar to device 1000 described in FIGS. 1A-B with the notable difference that device 2000 further includes a cannula rotating mechanism 2635 operatively coupled to a flexible hollow cannula ("cannula") 2600 of device 2000 to induce precession thereof.

Similarly to device 1000 of FIGS. 1A-B, device 2000 may include a distal casing section 2605, and a proximal casing section 2611. Cannula 2600 is at least partially movably housed within a guiding tube 2602 and at least partially houses a flexible wire 2614 configured to move therein, such as to protrude distally therefrom into the sinus cavity and to grind, chop and/or stir material present in the sinus cavity and/or inside cannula 2600. Flexible wire 2614 is shown herein as having a loop at a distal end thereof, which is an embodiment of a distal end of a wire (which is also termed "flexible wire" or "grinding wire") as disclosed herein. Other distal shapes or forms, such as, a curve in the wire for example an L shaped curve are also covered under the scope of this disclosure.

Optionally, as shown in FIGS. 2A and 2B, cannula rotating mechanism 2635 includes a dial 2640, and dial housing 2639. Optionally, dial 2640 is operatively coupled to cannula 2600 and induces precession of cannula 2600. Dial 2640 may be directly or indirectly coupled to cannula 2600. In a non-limiting example, precession of cannula 2600 may facilitate cannula insertion into patient sinus. Optionally, dial housing 2639 is coupled to proximal casing section 2611. Optionally, dial housing 2639 includes an opening in device casing 2611 that enable the user to rotate dial 2640 using his/her finger. According to some embodiments, device 2000 is configured to enable the user to hold gripping handle 1609, such that two three or four fingers may conveniently interface with a distal surface of distal gripper 1609a and/or a thumb may conveniently interface with dial 2640, and/or index finger lay on cannula handle 1608, and/or such that one, two or three fingers grasp syringe 1610.

According to some embodiments, dial 2640 comprises rotation marks, such as 0-360 degrees marks. According to some embodiments, the rotation marks provide the user an indication about the cannula's 2600 distal tip 2629 bending orientation in space. According to some embodiments, the user may use dial 2640, cannula handle 2607, cannula advancement marks 2605 and the rotation marks to direct distal tip 2629 of cannula 2600 and wire 2614 rotation to and from desired locations in the sinus cavity. According to some embodiments, the user may direct the rotation of wire 2614 towards the sinuses medial side. According to some embodiments, the user may direct the rotation of wire 2614 away from potential nerves, blood vessels and/or other hazardous structures in the sinuses and/or ear cavity.

According to some embodiments, device 2000 may include a motor grasping mechanism such as a motor grasping handle 2670 or an o-ring 2672. Motor grasping mechanism is configured to connect the motor 2613 to wire handle 2612 or to device casing 2611. According to some embodiments, wire handle 2612 and casing 2611 comprises rails 2675 for orientation and smooth movement of handle 2612 within casing 2611. According to some other embodiments, motor 2613 may function as a handle as well as a motor. In such case motor 2613 and casing 2611 comprise rails 2675 for orientation and smooth movement of motor 2613 within casing 2611.

Figure 3A:
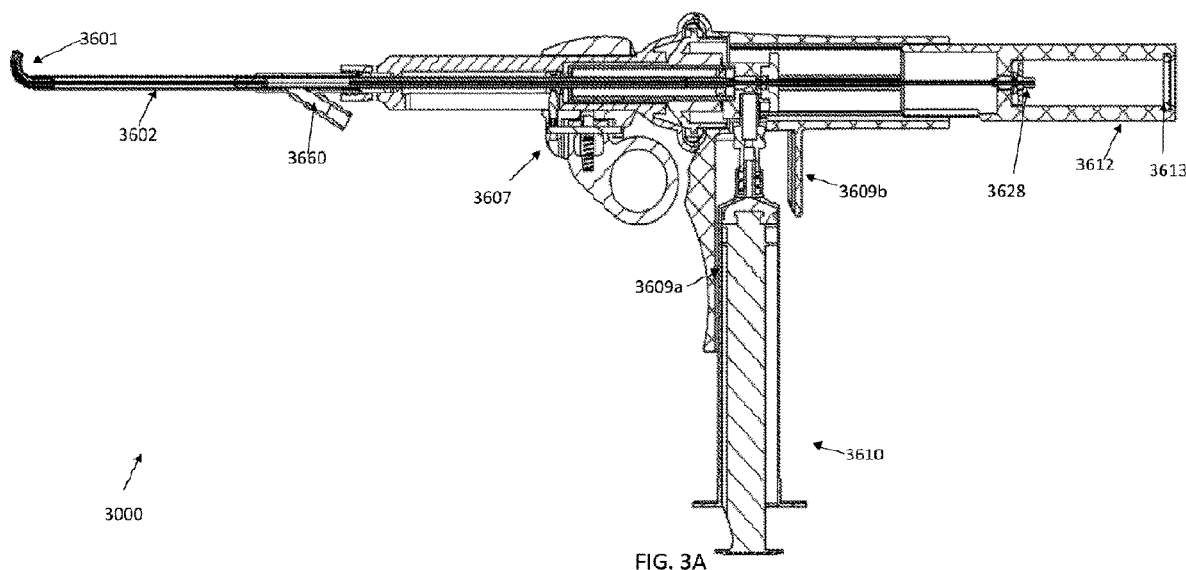
FIGS. 3A-3C schematically illustrate a longitudinal cross sectional view of a device for treating a paranasal sinus condition in retracted, partially opened, and opened configurations, respectively, according to some embodiments.
Figure 3B:
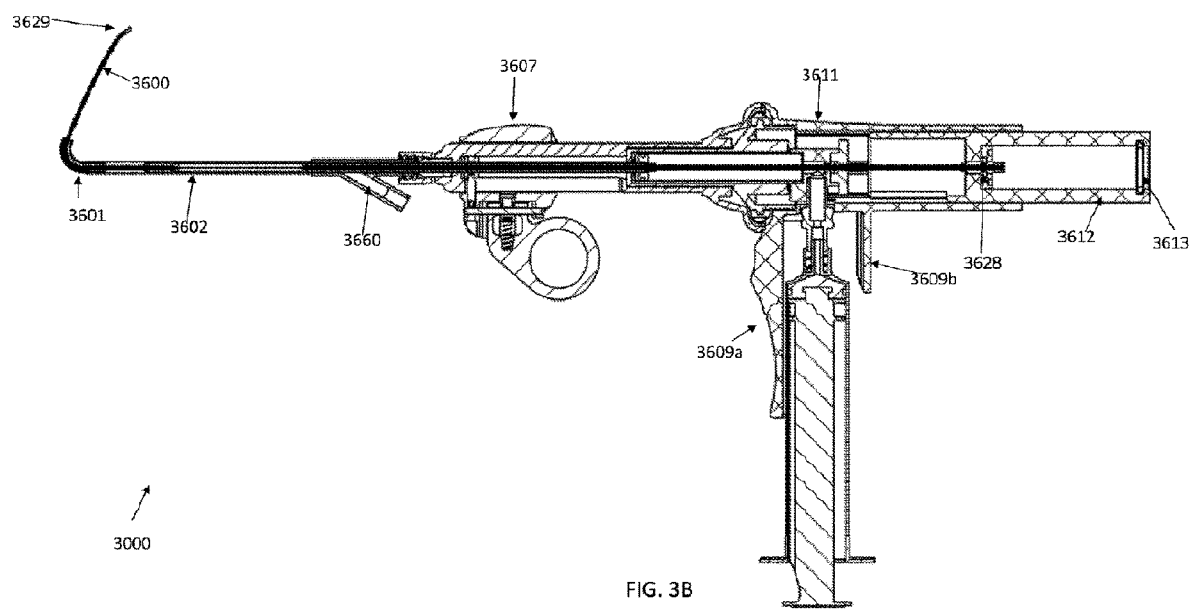
Figure 3C:
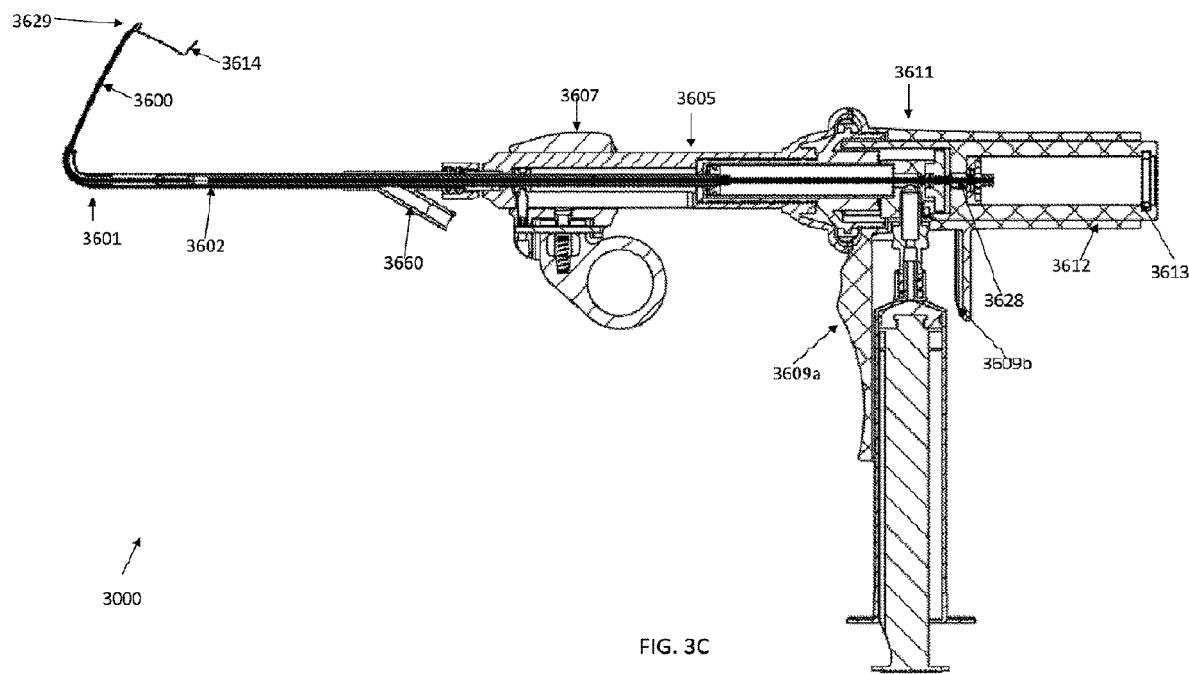

Reference is now made to FIGS. 3A, 3B, 3C which illustrate longitudinal cross sectional views of a device 3000 (which is substantially similar to device 2000 described in FIGS. 2A-B) that may be used for treating a paranasal sinus condition in a retracted, partially opened and opened configurations, respectively, and to FIGS. 3D, 3E, 3F and 3G which show enlargements of a distal section, a distal middle section, a proximal middle section and a proximal section of device 3000 in its opened configuration, respectively, according to some embodiments.

Device 3000 is substantially similar to device 2000 described in FIGS. 2A-B with the notable difference that device 3000 further includes an aspiration channel 3660 operably coupled to a guiding tube 3602 of device 3000 and facilitates aspiration of liquids from a sinus opening. As a non-limiting example, washing liquids applied into the sinus cavity by device 3000 via cannula 3600 may be aspirated via aspiration channel 3660 of device 3000 as it flow out of the sinus opening around cannula 3600 body. Cannula 1600 ends with a distal tip 3629, which may be atraumatic and/or may be closed. Optionally, wire 3614 protrudes out of a side wall of cannula 3600.

Similarly to device 2000 of FIGS. 2A-B, device 3000 may include a distal casing section 3605, and a proximal casing section 3611. A guiding tube 3602 of device 3000 at least partially houses a flexible hollow cannula ("cannula") 3600 movable therein, and a flexible wire 3614 which is movable within cannula 3600.

Figure 3D:
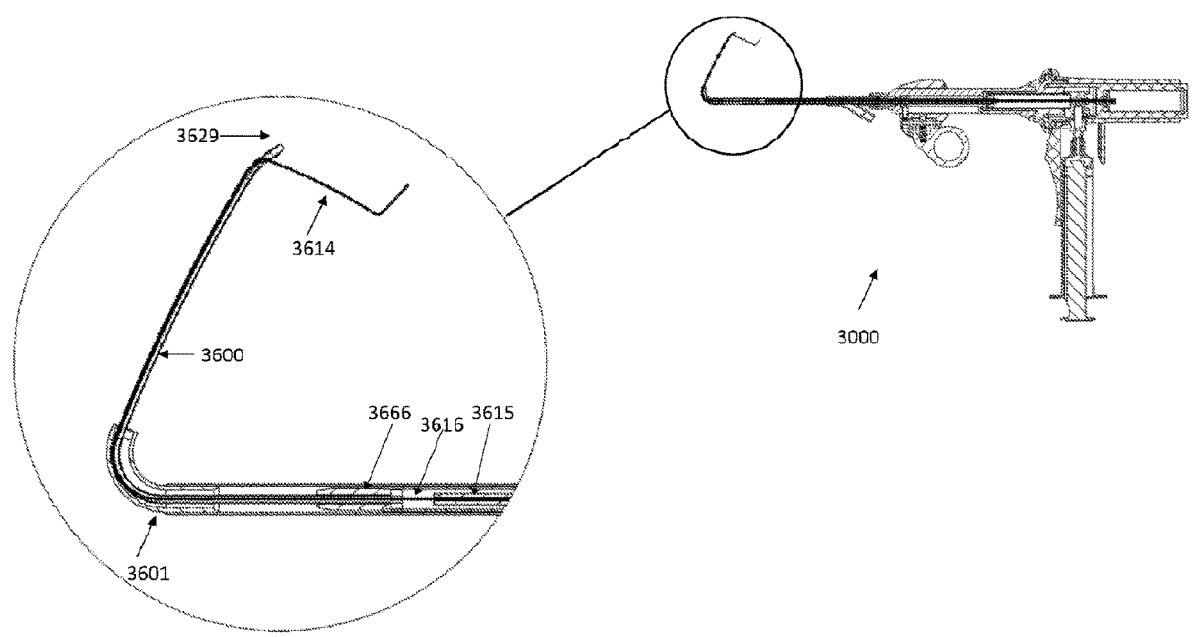
FIG. 3D shows an enlargement of a distal portion of the device FIG. 3C, according to some embodiments.

Cannula 3600 is coupled, at a proximal section thereof, to a liquid tube 3616, which is operably coupled to an irrigation/aspiration source for flowing liquids there through. Optionally, cannula 3600 and liquid tube 3616 are interconnected by a cannula connector 3666 positioned within a central lumen of guiding tube 3602 (as best shown in FIG. 3D) According to some embodiments, liquid tube 3616 is stiffer than the cannula. A diameter of a central lumen extending through liquid tube 3616 is larger than a diameter of a central lumen extending through cannula 3600 to facilitate a decrease of flow resistance for liquids therethrough. A diameter of a central lumen extending through liquid tube 3616 is larger than a diameter of a central lumen extending through cannula 3600 by at least about 1 mm, 2 mm, 3 mm, 4 mm, or 5 mm Each possibility represents a separate embodiment.

Wire 3614 extends within cannula 3600 and liquid tube 3616. Optionally, wire 3614 is coupled, at a proximal section thereof, to a wire transmission shaft ("shaft") 3615. Shaft 1615 extends from a connecting point with wire 3614, proximally to a wire handle 3612 and/or a motor 3613. A distal part of shaft 3615 is located within the liquid tube 3616. Optionally, operation of motor 3613 induces rotation of shaft 3615 which transmits rotation movement to wire 3614. Shaft 3615 has a larger diameter than wire 3614. According to some embodiments, shaft 3615 is stiffer and has higher torqueability and fatigue resistance than wire 3614. Optionally, wire handle 3612 moves wire 3614 proximally and distally within device 3000 by moving shaft 3615 which is coupled thereto. Wire handle 3612 may include a connector 3628, that connects distal rotating end of motor 3613 and shaft 1615 (as best shown in FIG. 3G). According to some embodiments, a proximal end of connector 3628 and a distal end of motor 3613 have matching shapes such as in Allen key. According to some embodiments, the proximal end of connector 3628 and the distal end of motor 3613 have magnetic connection or coupling. According to some embodiments, the proximal end of connector 3628 and/or the distal end of motor 3613 include an alignment mechanism 3680, such as a bearing. Optionally, wire handle 3612, and/or casing 3611 are shaped to grasp at least a portion of the motor body (e.g., the non-rotating part of the motor).

Optionally, an element in the distal end of cannula connector 3666 or in the shaft 3615 such as a socket, a bulb or a protrusion (not shown) prevents cannula 3600 occlusion by wire transmission shaft 3615 when it is advanced forward (distally) by a wire handle 3612.

In FIG. 3A, device 3000 is presented in a position similar to device 1000 in FIG. 1A, where cannula 3600 and wire 3614 are both fully proximally retracted, such that wire 3614 is positioned inside cannula 3600 and does not protrude therefrom, and cannula 3600 is positioned inside guiding tube 3602 and does not protrude therefrom. Cannula handle 3607 and wire handle 3612 are both fully proximally retracted.

In FIG. 3B, device 3000 is presented in a position where cannula 3600 protrudes from distal end 3601 of guiding tube 3602 while wire 3614 extends distally, pulling handle 3612 distally. It is still positioned inside cannula 3600 and does not protrude from a distal end of cannula 3600. In order to reach such configuration, cannula handle 3607 was moved distally by a user (allowing cannula 3600 to protrude from distal end 3601 of guiding tube 3602) while wire handle 3612 was only partially distally pulled. Optionally, Liquid tube 3616 and shaft 3615 are linked such that a proximal/distal movement of cannula handle 3607 is transmitted to a movement of wire 3614, shaft 3615 and wire handle 3612 in the same direction as cannula 3600. The linkage enables to keep wire 3614, in its relative position within cannula 3600 as the cannula is moving forward. Such a movement may enable using a shorter cannula with less flow resistance and a shorter device. Full movement of wire handle 3612 backward, will also mediate a proximal movement of cannula 3600 and cannula handle 3607. According to some embodiments, liquid tube 3616 and shaft 3615 linking mechanism may be a ring 3690 around shaft 3615 body that may be pulled by a narrowing structure 3695 in liquid tube 3616 inner lumen or by its distal end.

In FIG. 3C, device 3000 is presented in a position similar to device 1000 in FIG. 1B, where cannula 3600 fully protrudes from distal end 3601 of guiding tube 3602 and wire 3614 extends distally and protruding from a distal end of cannula 3600. In order to reach such configuration, wire handle 3612 was moved distally by a user (distally pushing wire 3614 via shaft 3615 to protrude from the distal end 3601 of cannula 3600). In this configuration both cannula 3600 and wire 3614 are fully distally extending from device 3000. This configuration may also be referred to as an opened position of device 3000. Cannula 3600, liquid tube 3616, wire 3614 and the wire transmission shaft 3615 are advanced forward so cannula 3600 is protruding out of guiding tube distal end 3601, the wire 3614 is protruding out of the cannula 3600, and wire transmission shaft 3615 is located within the liquid tube 3616 inside guiding tube 3602.

Figure 3E:
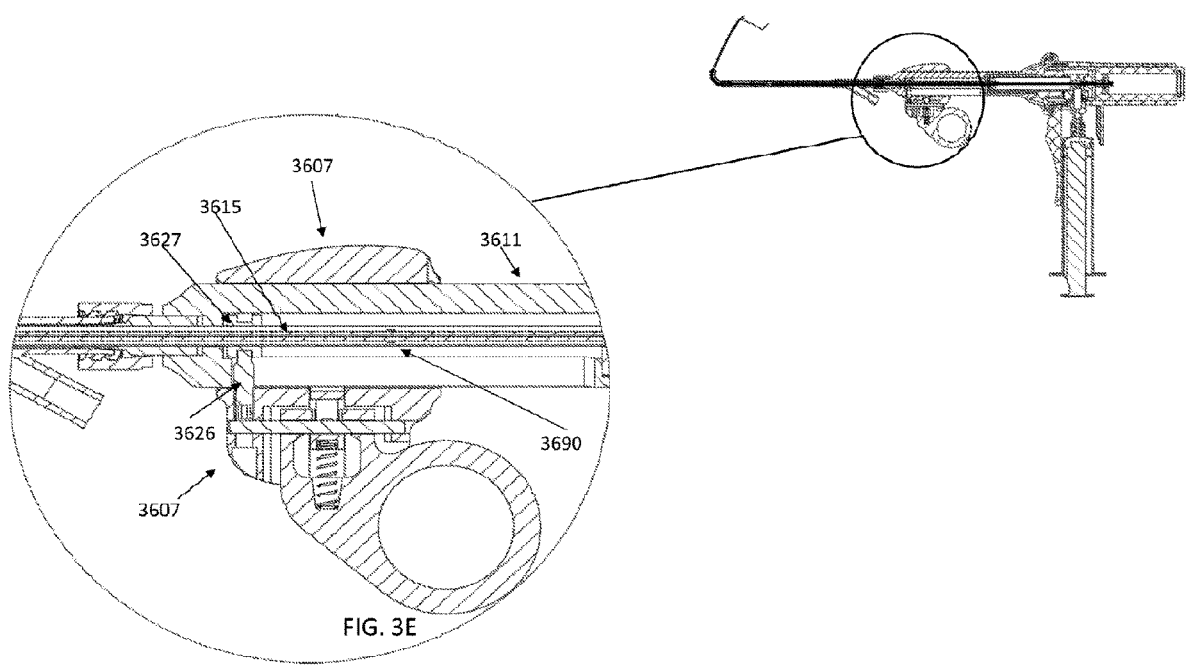
FIG. 3E shows an enlargement of a portion of the device FIG. 3C, according to some embodiments.
Figure 3F:
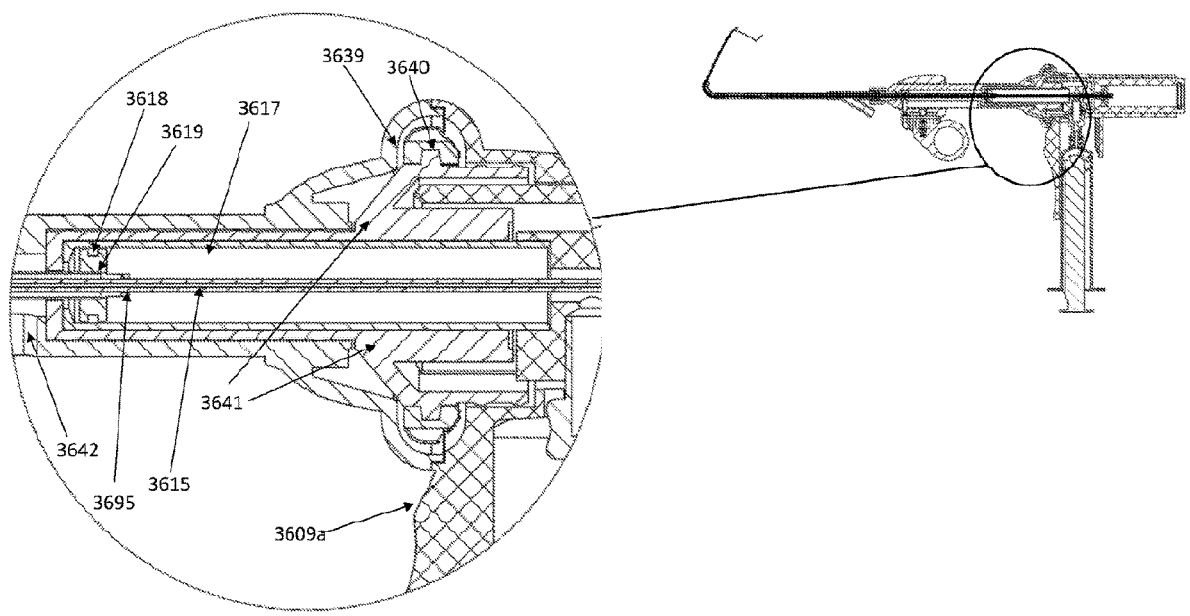
FIG. 3F shows an enlargement of a portion of the device FIG. 3C, according to some embodiments.
Figure 3G:
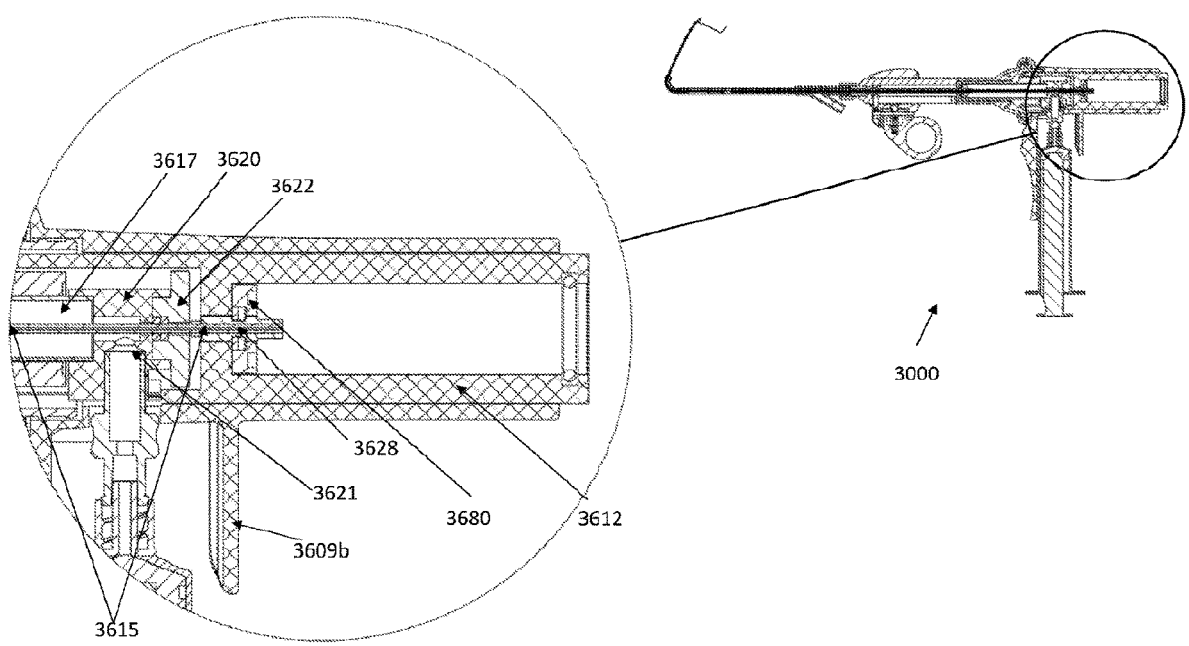
FIG. 3G shows an enlargement of a proximal portion of the device FIG. 3C, according to some embodiments.

Reference is now made to FIG. 3E, which shows an enlargement of a cannula handle portion of device 3000 of FIG. 3C (in an opened position), according to some embodiments, to FIG. 3F, which shows an enlargement of a middle portion of device 3000 of FIG. 3C (in an opened position), According to some embodiments, and to FIG. 3G, which shows an enlargement of a proximal portion of device 3000 of FIG. 3C (in an opened position), according to some embodiments.

In a middle section of device 3000, exists a T intersection 3620. According to some embodiments, the number of tubes in T intersection 3620 is three or more. On its distal side T intersection 3620 is connected to the liquid tube 3616. On its middle side T intersection 3620 is connected to a syringe 3610, or to other type of irrigation/aspiration lines. Wire transmission shaft 3615 reaches T intersection 3620 from a proximal side thereof and extends from its proximal side to its distal side (into the liquid tube 3616).

In order to enable simultaneously irrigation/aspiration and wire 3614 rotation T intersection 3620 must be sealed to fluids and air from all its tubes. Therefore, according to some embodiments, T intersection 3620 includes three seals around it: a cannula seal (may also be referred to as a liquid tube seal, or movable seal) 3618 (as best shown in FIG. 3F) is sealing T intersection 3620 from its distal side. A syringe seal (may also be referred to as an irrigation/aspiration seal) 3621, is sealing the T intersection 3620 from its middle side. A wire transmission shaft seal (may also be referred to as a wire seal, or a wire/shaft seal or a dynamic seal) 3622, is sealing the T intersection 3620 from its proximal side. A syringe seal 3621 is sealing the T intersection 3620 from its middle side.

According to some embodiments, cannula seal 3618 is surrounding part of the liquid tube 3616. According to some embodiments, cannula seal 3618 is positioned within defined lumen 3617. Optionally, lumen 3617 includes a distal and proximal ends and its shape is fitted to cannula seal 3618 shape, such that no air or undesired liquids can penetrate to or escape liquid tube 3616. Optionally, cannula seal 3618 is proximally and distally movable within lumen 3617. According to some embodiments, cannula seal 3618 is attached to liquid tube 1616. Cannula seal 3618 may be made of flexible material such as rubber of soft plastic as in syringe pistons. According to some embodiments, cannula seal 3618 is made of syringe piston (or a structure similar thereto) and lumen 3617 is made of syringe body (or a structure similar thereto). According to some embodiments, cannula seal 3618 is made of one or more O-rings. According to some embodiments, cannula seal 3618 is surrounding a housing 3619 that is attached to the liquid tube 3616. Housing 3619 is configured to prevent unintended migration of cannula seal 3618. According to some embodiments, the cannula seal 3618 seals the liquid tube 3616 both during movement forward and backward and during liquid tube 3616 and cannula 3600 rotation.

Acceding to some embodiments, syringe seal 3621 may be connected to one or more syringes. According to other embodiments syringe seal 3621 may be connected to irrigation/aspiration line or lines (not necessarily syringe(s) as the name implies), such as motorized suction/irrigation machine, sampling vials etc. Syringe seal 3621 is configured to seal the connection between the irrigation/aspiration lines (such as, but not limited to, a syringe) and T intersection 3620. Acceding to some embodiments, syringe seal 3621 may enable syringe/irrigation/aspiration lines replacement during the procedure. Acceding to some embodiments, a user may use one syringe for initial sinus irrigation (such as with saline) and mucus sampling, and one or more additional syringes for irrigation with therapeutic substance. Acceding to some embodiments, syringe seal 3621 may be in a form of a locking luer. Acceding to some embodiments, syringe seal 3621 may be fitted only for certain syringes/tubes/vials, depending on the need. This feature may prevent mistakes such as using the wrong syringe for a certain procedure. Acceding to some embodiments, syringe seal 3621 and/or device gripping handle distal end 3609a and/or device gripping handle distal end 3609b may prevent the user from using unintended syringe such as too big syringe by miss-fitting unintended syringe geometric properties.

Wire seal (which may also be referred to as a shaft seal, wire transmission shaft seal or dynamic seal) 3622 is configured to seal the connection between T intersection 3620 and motor 3613. Wire seal 3622 also enable transmission of rotation movement from motor 3613 to wire transmission shaft 3615 and or wire 3614. According to some embodiments, Wire seal 3622 enables transmission of rotation movement from motor 3613 to wire transmission shaft 3615 and or wire 3614, and simultaneously sealing connection between T intersection 3620 and motor 3613. According to some embodiments, wire seal 3622 enables sealing under a rotation movement in (RPM) equal or greater than about 100 rounds per minute (RPM), 500 RPM, 1000 RPM, 5,000 RPM, 10,000 RPM, 15,000 RPM, for example, about 500-1500 RPM, 1000-5000 RPM, 4000-7000 RPM, 7500-12,000 RPM. Each possibility represents a separate embodiment. According to some embodiments, wire transmission shaft 3615 is movable back and forward (proximally and distally) trough wire seal 3622. Suitable seal types include, but are not limited to, dynamic seal, labyrinth seal and magnetic seal.

According to some embodiments, wire seal 3622 includes one or more O-rings that surrounds wire transmission shaft 3615. According to some embodiments, the O-ring(s) press on wire transmission shaft 3615. According to some embodiments, the O-ring(s) are being pressed on wire transmission shaft 3615 by its environment. According to some embodiments, the O-ring(s) are lubricated or self-lubricated.

According to some embodiments, device 3000 further includes a mechanism that connects cannula handle 3607 to liquid tube 3616 as it move together back and forth, but enable the liquid tube to rotate around its axis. According to some embodiments, pin 3626 connect cannula handle 3607 to liquid tube 3616. According to some embodiments, connection of pin 3626 to liquid tube 3616 is by liquid tube surrounding ring or wider part in the liquid tube. According to some embodiments, the connection between pin 3626 to liquid tube 3616 is linear, when one is being advanced or retrieved the other one is also being advanced or retrieved the same distance. According to some embodiments, pin 3626 can also move forward (distally) the wire transmission shaft 3615. Pin 3626 is protruding via liquid tube 3616, and it is fitted to push a ring 3627 located around liquid tube 3616.

A dial 3640 is shown in FIG. 3F, according to some embodiments, dial 3640 is located within dial housing 3639. Optionally, dial 3640 is operatively coupled to cannula 3600 and induces precession of cannula 3600 at a distal end thereof. Dial 3640 may be operatively coupled to cannula 3600 via liquid tube 3616, and precession of liquid tube 3616 transmits precession movement to cannula 3600. Optionally, rotation of dial 3640 induces precession of liquid tube 3616 which transmits precession movement to cannula 3600. Alternatively, dial 3640 may be directly coupled to cannula 3600.

Dial housing 3639 includes an aperture for the user finger that allows dial 3640 rotation. According to some embodiments, a dial interior part 3641 connects dial 3640 to liquid tube 3616, which is connected to cannula 3600. According to some embodiments, a connection apparatus 3642 between dial 3660 and liquid tube 3616 enables cannula 3600 rotation with dial rotation and longitudinal movement of the liquid tube 3616 without longitudinal movement of the dial. According to some embodiments, a connection apparatus 3642 between dial interior part 3641 and liquid tube 3616 can be a protrusion and a socket. According to some embodiments, connection apparatus 3642 includes a long protrusion along the liquid tube 3616 and a fitted socket in round dial interior part 3641, such that the socket may move along the long protrusion. According to some embodiments, connection apparatus 3642 is located distally to the movable cannula seal 3618. According to some embodiments, dial interior part 3641 may stretch or extend its length within device casing 3611 and over cannula seal 3618.

According to some embodiments, shaft 3615 may include several friction and/or vibrating reduction mechanisms that reduce its friction and/or vibration against liquid tube 3616. According to some embodiments, the mechanisms may be bearings, such as alignment mechanism 3680 or the motor bearing in the motor distal end. According to some embodiments, the mechanism, such as alignment mechanism 3680 may include a low friction surface such as Teflon washers. According to some embodiments, the mechanism may be a narrowing in liquid tube 3616 that centers shaft 3615 with the center of liquid tube 3616 According to some embodiments, the narrowing, such as narrowing structure 3695 in liquid tube 3616 is configured to center the shaft and allow liquid flow in the liquid tube. According to some embodiments, wire transmission shaft seal 3622 also may serve as a friction and/or vibrating reduction mechanism. According to some embodiments, device 3000 may include at least 2, 3, 4 friction and/or vibrating reduction mechanisms, each represent a separate embodiment.

Figures 4A, 4B:
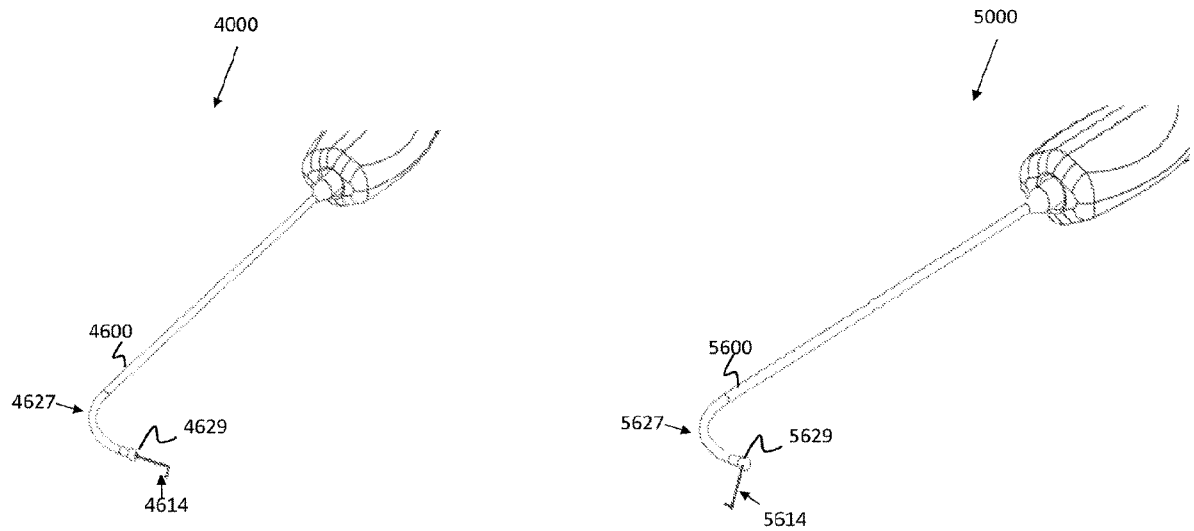
FIG. 4A shows a distal portion of a device for treating a paranasal sinus, according to some embodiments.
FIG. 4B shows a distal portion of a device for treating a paranasal sinus, according to some embodiments.

Reference is now made to FIG. 4A, which shows a distal portion of a device 4000 that may be used for treating a paranasal sinus condition in an open configuration, according to some embodiments. Device 4000 includes a stiff bent cannula 4600 and a wire 4614. Cannula 4600 includes a curved distal section 4627 shaped to allow/facilitate insertion into a sinus of a patient. Optionally, the insertion is into a maxillary sinus, a frontal sinus, a sphenoid sinus, or Eustachian tubes. Each possibility represents a separate embodiment, and may be combined at will. According to some embodiments, cannula 4600 might be bent to angles of 110°-90° for the maxillary sinus, 0-30° for the sphenoid sinus, 60°-80° for the frontal sinus, 30°-70° for the Eustachian tubes. According to some embodiments, the cannula 4600 is bendable using a jig or via the user hands. According to some embodiments, the cannula 4600 is made of a malleable material as steel.

According to some embodiments, cannula 4600 is operably coupled to aspiration machine or to a syringe, such as syringe 1610 of FIGS. 1A-B. According to some embodiments, such coupling is via a liquid tube such as liquid tube 3616 of FIGS. 3A-G. According to some embodiments, wire 4614 is connected to a motor such as motor 1613 of FIGS. 1A-B. According to some embodiments, such connection is via a shaft, such as shaft 3615 of FIGS. 3A-G. According to some embodiments, the movement of wire 4614 and a shaft such as shaft 3615 forward and backward is controlled by a wire handle, such as wire handle 3612 of FIGS. 3A-G. According to some embodiments, device 4000 may have a casing and a grip handle such as 1605, 1611, 1609*a-b* of FIGS. 1A-B. According to some embodiments, device 4000 may have sealing mechanisms such as seals 3620 and 3622 of FIG. 3A-G. According to some embodiments, device 4000 may have bearing mechanisms similar to of device 3000 such as 3628 of FIGS. 3A-G.

Wire 4614 is configured is at least partially housed within cannula 4600 and configured to distally protrude therefrom. Wire 4614 may be configured to rotate within curved distal section 4627 during sinus irrigation and/or sinus aspiration via curved distal section 4627. Wire 4614 may be configured to protrude out of curved distal section 4627 and rotate. According to some embodiments, rotating wire 4614 protrude out of atraumatic distal tip 4629. According to another embodiment, as demonstrated in FIG. 4B a rotating wire 5614 protrusion out of a curved distal section 5627 or atraumatic distal tip 5629 of cannula 5600 is a side fire protrusion.

Figure 4C:
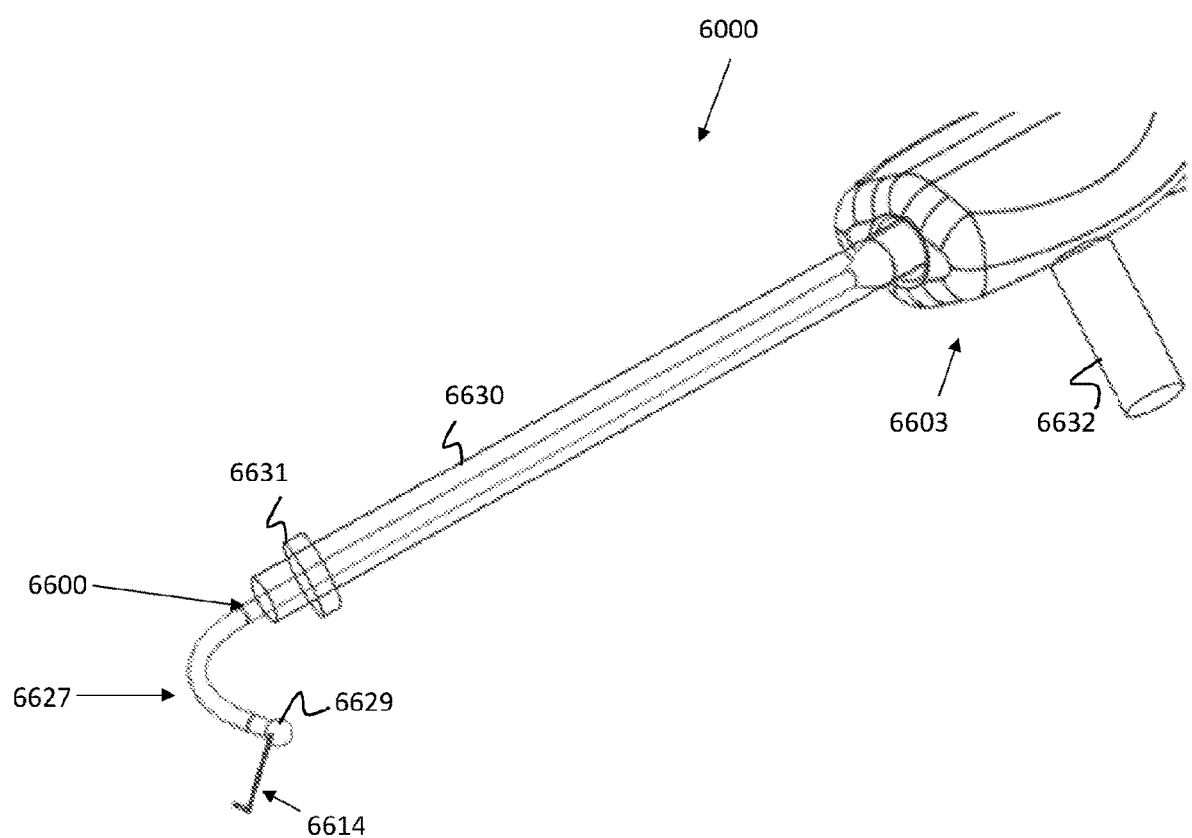
FIG. 4C shows a distal portion of a device for treating a paranasal sinus, according to some embodiments.

Reference is now made to FIG. 4C, which shows a distal portion of a device 6000 that may be used for treating a paranasal sinus condition in an opened configuration, according to some embodiments. Device 6000 is substantially similar to device 4000, with the notable difference that a cannula 6600 of device 6000 is at least partially housed by an aspiration tube 6630 configured for aspiration of fluids (e.g., liquids spilled out of the sinus). Similarly to device 4000, device 6000 includes cannula 6600 and a wire 6614. Wire 6614 may protrude laterally out of a curved distal section 6627 of cannula 6602 or an atraumatic distal tip 6629 thereof.

Optionally, aspiration tube 6630 such as guiding tube 6302 of FIG. 3A-G is operably coupled to a second aspiration line such as aspiration machine or to a syringe, such as aspiration channel 3660 of FIGS. 3A-G. Optionally, a connector 6603 having a T or Y shape interconnects aspiration tube 6630 and second aspiration tube 6632. Optionally, curved distal section 6627 of cannula 6600 protrudes distally from aspiration tube 6630. In a non-liming example, curved distal section 6627 may be at least partially inserted into a patient sinus or Eustachian tube, while aspiration tube 6630 is not inserted into the sinus or Eustachian tube. Optionally, cannula 6600 may provide irrigation and or aspiration via distal curved section 6627 while aspiration tube 6630 is operated to aspirate liquids spilled out of the sinus. In a non-limiting example, irrigation and/or aspiration is provided through distal curved section 6627 and aspiration tube 6630 is operated to aspirate the liquids spilled out of the sinus while rotating wire 6614 may be rotated within distal curved section 6627 and/or within the sinus cavity.

According to some embodiments, aspiration tube 6630, connector 6603 and/or second aspiration tube 6632 includes a syphon mechanism to collect aspirated liquids or specimens from the sinus. Optionally, a distal end of aspiration tube 6630 is atraumatic. A distal portion of aspiration tube 6630 may include an element 6631 made of soft material and or collapsible construction such as foam. Optionally, element 6631 circumferentially surrounds the distal end of tube 6630. Optionally, element 6631 is shaped as a ring and positioned proximally to the distal end of aspiration tube 6630. Optionally, element 6631 may be attached to the sinus ostium during sinus irrigation and aspiration. According to some embodiments, element 6631 may seal the sinus opening during irrigation and may prevent irrigation liquid flow from the sinus to the nasal cavity.

Figure 5A:
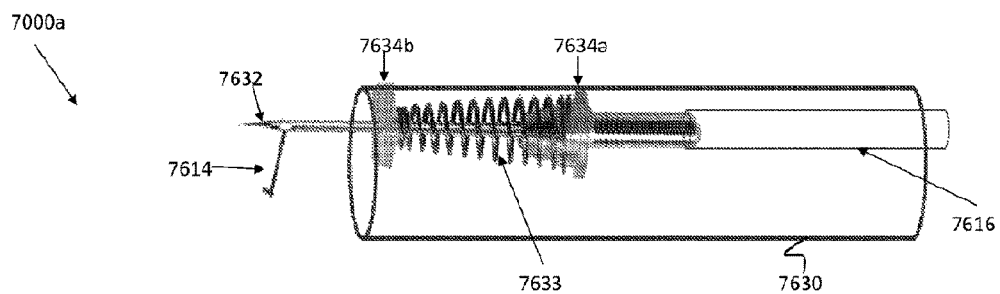
FIG. 5A shows a partially transparent view of distal portion of a device for treating a paranasal sinus, according to some embodiments.

Reference is now made to FIG. 5A which shows a distal portion of a device 7000a that may be used for treating a paranasal sinus condition in an opened configuration, according to some embodiments. A needle 7632 is positioned within an aspiration tube 7630. According to other embodiments (not shown here) needle 7632 may be mounted on or positioned within a cannula such as cannula 6600 of FIG. 4C or a distal section thereof such as 6627 of FIG. 4C. Optionally, wire 7614 is aligned to fit within needle 7632 and assumes a predefined shape upon protrusion distally therefrom. Optionally, device 7000a further includes a spring 7633 and spring stopping mechanism 7634a and 7634b configured to press and advance needle 7632 into the sinus wall. Stopping mechanism 7634a and 7634b may limit needle 7632 advancement into the sinus to the distance defined between 7634a and 7634b. Needle 7632 may be coupled to a liquid tube 7616, to allow a user to irrigate and aspirate the sinus via needle 7632, optionally, during wire 7614 rotation. In a non-limiting example, the user irrigates the sinus via needle 7632 and liquid tube 7616, during wire 7614 rotation and aspirate the spilling liquids via aspiration tube 7630.

According to some embodiments, device 7000a has similar mechanisms to device 6000 except of the needle 7632 is replacing cannula 6600.

According to some embodiments, device 7000a has similar mechanisms to device 3000, except from the needle 7632 is that replacing cannula 3600, the lack of cannula actuation and sealing mechanisms, and the aspiration tube 7630 that replace guiding tube 3602. According to some embodiments, needle 7632 is operably coupled to aspiration machine or to a syringe, such as syringe 1610 of FIGS. 1A-B. According to some embodiments, such coupling is via a liquid tube such as liquid tube 3616 of FIGS. 3A-G. According to some embodiments, wire 7614 is connected to a motor such as motor 1613 of FIGS. 1A-B. According to some embodiments, such connection is via a shaft, such as shaft 3615 of FIGS. 3A-G. According to some embodiments, wire 7614 and shaft (such as shaft 3615 3615 of FIGS. 3A-G movement forward and backward is controlled by a wire handle, such as wire handle 3612 of FIGS. 3A-G. According to some embodiments, device 7000a may have a casing and a grip handle such as 1605, 1611, 1609a-b of FIGS. 1A-B. According to some embodiments, device 7000a may have sealing mechanisms such as seals 3620 and 3622 of FIGS. 3A-G. According to some embodiments, device 7000a may have bearing mechanisms similar to connector 3628 of device 3000 of FIGS. 3A-G.

Figure 5B:
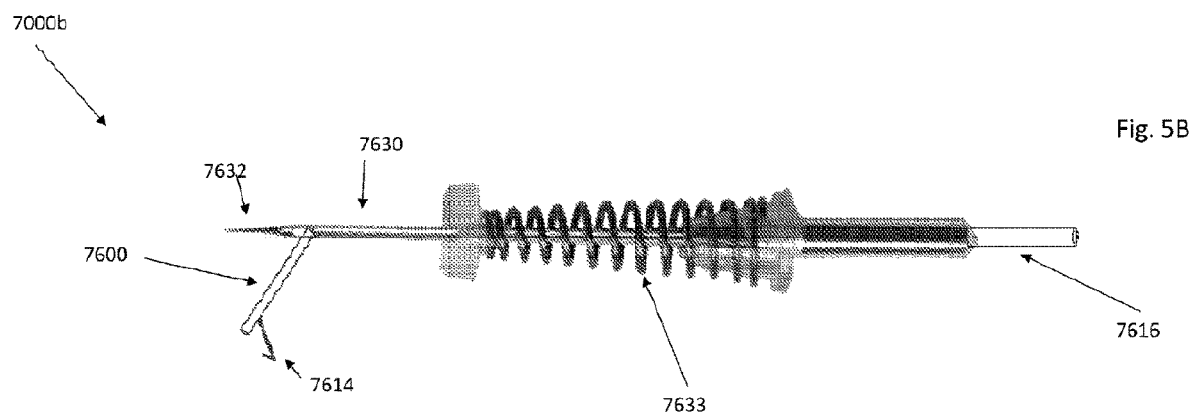
FIG. 5B shows a partially transparent view of distal portion of a device for treating a paranasal sinus, according to some embodiments.
Figures 6A, 6B, 6C, 6D:
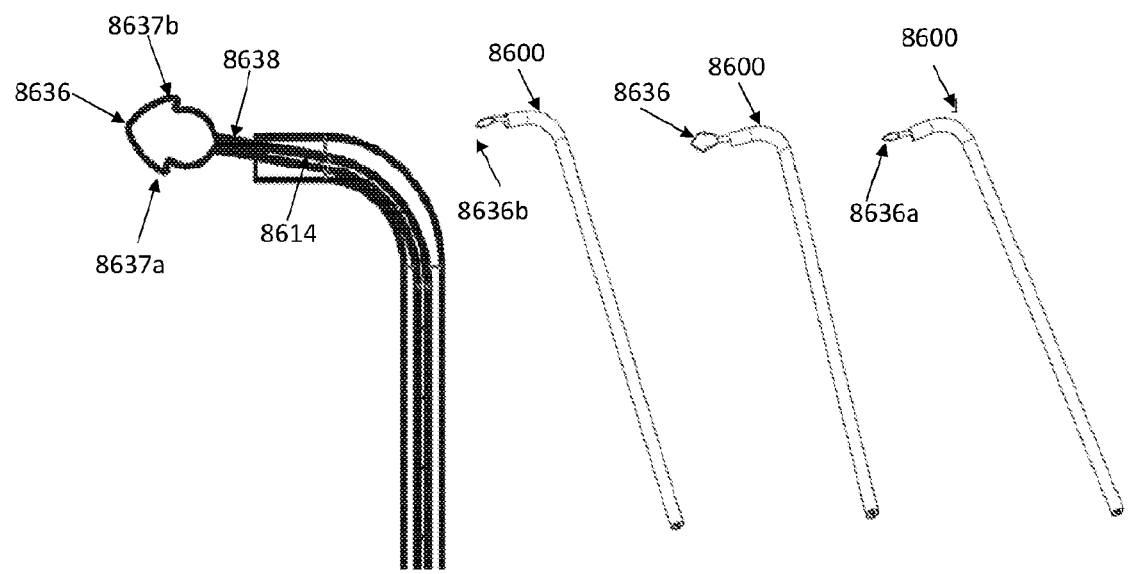
FIG. 6A shows a partially transparent view of a distal end of a cannula of a device for treating a paranasal sinus condition and a wire protruding distally therefrom in an opened configuration, according to some embodiments.
FIG. 6B shows a distal end of a cannula of a device for treating a paranasal sinus condition and a wire protruding distally therefrom in an opened configuration, according to some embodiments.
FIG. 6C shows a perspective view of the distal end of the cannula of FIG. 6A, according to some embodiments.
FIG. 6D shows a distal end of a cannula of a device for treating a paranasal sinus condition and a wire protruding distally therefrom in an opened configuration, according to some embodiments.

Reference is now made to FIG. 5B, which shows a distal portion of a device 7000b that may be used for treating a paranasal sinus condition in an opened configuration, according to some embodiments. According to some embodiments, a cannula 7600 is protruding out of a distal tip of needle 7632. According to some embodiments, device 7000b has similar mechanisms to device 3000, except for needle 7632 instead of distal end 3601 of guiding tube 3602. According to some embodiments, cannula 7600 is operably coupled to aspiration machine or to a syringe, such as syringe 1610 of FIGS. 1A-B. According to some embodiments, such coupling is formed via a liquid tube such as liquid tube 3616 of FIGS. 3A-G. According to some embodiments, wire 7614 is connected to a motor such as motor 1613 of FIGS. 1A-B. According to some embodiments, such connection is formed via a shaft, such as shaft 3615 of FIGS. 3A-G. According to some embodiments, wire 7614 and shaft 3615 movement forward and backward is controlled by a wire handle, such as wire handle 3612 of FIGS. 3A-G. According to some embodiments, device 7000b may have a casing and a grip handle such as 1605, 1611, 1609a-b of FIGS. 1A-B. According to some embodiments, device 7000b may have sealing mechanisms such as seals 3620 and 3622 of FIGS. 3A-G. According to some embodiments, device 7000b may have similar bearing mechanisms to device 3000 such as 3628 of FIGS. 3A-G.

Reference is now made to FIGS. 8A, 8B, 8C, and 8D which show a distal portion of a cannula 8600 of a device 8000 that may be used for treating a paranasal sinus condition, each according to a different embodiment.

Referring to FIGS. 8A and 8C, a nitinol loop 8636 protrudes from a distal end of cannula 8600. Nitinol loop 8636 may include curves, bulbs or protrusions such as protrusions 8637a and 8637b that prevents it from retrieving into cannula 8600. Optionally, a metal crimp 8638 interconnects nitinol loop 8636 and a wire 8614.

Referring to FIG. 8B, a nitinol loop 8636b which protrudes from a distal end of cannula 8600 may include an offsite angle portion and may be rotated to facilitate its insertion into the sinus opening, such as by a motor (e.g., motor 1613 of FIGS. 1A and 1B).

Referring to FIG. 8D, a nitinol loop 8636a partially protrudes from a distal end of cannula 8600 and may be utilized as an atraumatic tip for cannula 8600.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions. It is understood that certain elements or configurations illustrated in a specific figure/embodiment may be included in other figures/embodiment and that various combination of elements and/or configurations are possible.

What we claim is:

1. A medical device for treating and/or diagnosing a sinus and/or ear condition, said medical device comprising:
   a housing comprising or functionally connected to:
      a hollow cannula defining a lumen extending at least partially along a length thereof, the hollow cannula is configured to be at least partially inserted through an ostium into a sinus cavity/ear of a subject; and
      a flexible grinding wire movable within the cannula's lumen and configured to be inserted into and retrieved out of the sinus cavity through the cannula's lumen, and to rotate along a longitudinal axis thereof and thereby grind, chop and/or stir material present in said sinus cavity and/or inside said hollow cannula, wherein the hollow cannula is in fluid flow communication with an irrigation/aspiration source;
      a wire handle functionally connected to the wire, allowing a user to advance and retrieve the wire within the hollow cannula and into and out of the cannula lumen; and
      a shaft, wherein at a distal section thereof, the shaft is connected to the wire and at a proximal section thereof, the shaft is connected to a motor connected to the wire handle, wherein the motor provides rotational movement to the shaft, which transmits this movement to the wire;
      wherein the device is handheld by a gripping handle.

2. The device of claim 1, further comprising a hollow cannula handle functionally connected to the hollow cannula, allowing the user to advance and retrieve the hollow cannula into the sinus cavity or the ear.

3. The device of claim 2, further comprising a connector configured for replacing of guiding tubes.

4. The device of claim 1, further comprising a guiding tube configured to house the hollow cannula therein and bend the hollow cannula as it is being advanced forward, and direct a distal end of the hollow cannula towards a sinus opening.

5. The device of claim 4, further comprising a mechanism for changing an angle of the distal section of the guiding tube, to facilitate introduction of the hollow cannula to various sinus anatomies.

6. The device of claim 4, further comprising a side port in the guiding tube, wherein the side port is configured for instrumentation insertion through a distal end of the guiding tube.

7. The device of claim 6, wherein the side port is configured to serve as an aspiration port being in fluid flow connection with the distal end of the guiding tube, wherein the aspiration port is configured for suction of aspiration/irrigation fluid from the guiding tube.

8. The device of claim 4, further comprising visualization equipment located within or mounted on a distal tip of the guiding tube.

9. The device of claim 1, further comprising a curve in a distal tip of said hollow cannula and a hollow cannula rotating mechanism, configured to allow the user to rotate the distal tip of the hollow cannula around a longitudinal axis of the cannula, thus facilitate insertion of the hollow cannula into the sinus cavity.

10. The device of claim 1, further comprising a hollow trocar configured to house said hollow cannula therein, puncture a sinus wall, sinus floor or ear wall and facilitate insertion of said hollow cannula into the sinus/ear cavity.

11. The device of claim 1, wherein the hollow cannula is configured to puncture via an ear or a sinus wall or sinus floor as a trocar.

12. A medical device for treating and/or diagnosing a sinus and/or ear condition, said medical device comprising:
    a housing comprising or functionally connected to:
       a hollow cannula defining a lumen extending at least partially along a length thereof, the hollow cannula is configured to be at least partially inserted through an ostium into a sinus cavity/ear of a subject; and
       a flexible grinding wire movable within the hollow cannula's lumen and configured to be inserted into and retrieved out of the sinus cavity through the hollow cannula's lumen, and to rotate along a longitudinal axis thereof and thereby grind, chop and/or stir material present in said sinus cavity and/or inside said hollow cannula, wherein the hollow cannula is in fluid flow communication with an irrigation/aspiration source;
       a wire handle functionally connected to the wire, allowing a user to advance and retrieve the wire within the hollow cannula and into and out of the hollow cannula lumen;
       a shaft, wherein at a distal section thereof, the shaft is connected to the wire and at a proximal section thereof, the shaft is connected to a motor connected to the wire handle, wherein the motor provides rotational movement to the shaft, which transmits this movement to the wire; and
       a liquid tube connected at a distal section thereof to a proximal side of the hollow cannula and at a proximal section thereof to the irrigation/aspiration source, such that the liquid tube is in fluid flow connection with the hollow cannula and the irrigation/aspiration source, wherein an inner diameter of the liquid tube is larger than an inner diameter of the hollow cannula, and wherein at least part of the shaft is located within said liquid tube lumen;
       wherein the device is handheld by a gripping handle.

13. The device of claim 12, wherein the irrigation/aspiration source comprises a replaceable syringe, a syphon, and/or a liquid container.

14. The device of claim 12, further comprising a cannula/liquid tube seal located within a defined lumen within the housing and surrounding at least portion of the hollow cannula and/or liquid tube, such that the hollow cannula and/or liquid tube is distally/proximally movable within the lumen and relative to the handle grip while remaining the hollow cannula and/or the liquid tube cavity sealed from air inlet and liquid outlet during irrigation and aspiration, wherein the cannula/liquid tube seal is further configured to facilitate rotation of the cannula/liquid tube relative to the handle grip while the cannula/liquid tube remains sealed.

15. The device of claim 12, further comprising a seal surrounding at least portion of the flexible grinding wire and/or shaft and facilitating distal/proximal movement of the flexible grinding wire and/or shaft within and relative to the hollow cannula and/or the liquid tube, while maintaining the hollow cannula and/or the liquid tube sealed from air inlet and liquids outlet during irrigation and aspiration, wherein the seal is further configured to facilitate high RPM rotation of the flexible grinding wire and/or shaft within and relative to the hollow cannula and/or the liquid tube, while the hollow cannula and/or the liquid tube remains sealed.

16. The device of claim 12, further comprising an irrigation/aspiration seal configured for connection and/or detachment of irrigation/aspiration source to the hollow cannula and/or liquid tube in a sealed manner.

17. A medical device for treating and/or diagnosing a sinus and/or ear condition, said medical device comprising:
- a housing comprising or functionally connected to:
    - a hollow cannula defining a lumen extending at least partially along a length thereof, the hollow cannula is configured to be at least partially inserted through an ostium into a sinus cavity/ear of a subject; and
    - a flexible grinding wire movable within the hollow cannula's lumen and configured to be inserted into and retrieved out of the sinus cavity through the hollow cannula's lumen, and to rotate along a longitudinal axis thereof and thereby grind, chop and/or stir material present in said sinus cavity and/or inside said hollow cannula, wherein the hollow cannula is in fluid flow communication with an irrigation/aspiration source;
- a wire handle functionally connected to the wire, allowing a user to advance and retrieve the wire within the hollow cannula and into and out of the hollow cannula lumen;
- a shaft, wherein at a distal section thereof, the shaft is connected to the wire and at a proximal section thereof, the shaft is connected to a motor connected to the wire handle, wherein the motor provides rotational movement to the shaft, which transmits this movement to the wire;
- a liquid tube connected at a distal section thereof to a proximal side of the hollow cannula and at a proximal section thereof to the irrigation/aspiration source, such that the liquid tube is in fluid flow connection with the hollow cannula and the irrigation/aspiration source, wherein an inner diameter of the liquid tube is larger than an inner diameter of the cannula, and wherein at least part of the shaft is located within said liquid tube lumen; and
- a connector connecting between the liquid tube/cannula and the shaft/wire such that when the liquid tube/cannula is moved distally the shaft/wire will also be distally moved, for at least part of the liquid tube/cannula advancement;

wherein the device is handheld by a gripping handle.

* * * * *